(12) United States Patent
Cui

(10) Patent No.: US 7,658,930 B2
(45) Date of Patent: Feb. 9, 2010

(54) KIT FOR DETECTING THE ANTIBODY OF HCV AND ITS PREPARING METHOD

(75) Inventor: Peng Cui, Apartment 203, Building 5 LiYuan Garden, XueFu Road, NanShan District, Shenzhen, Guangdong 518052 (CN)

(73) Assignee: Peng Cui, Guangdong (CN)

( * ) Notice: Subject to any disclaimer, the term of this patent is extended or adjusted under 35 U.S.C. 154(b) by 0 days.

(21) Appl. No.: 11/883,506

(22) PCT Filed: Feb. 2, 2005

(86) PCT No.: PCT/CN2005/000149
§ 371 (c)(1), (2), (4) Date: Oct. 9, 2008

(87) PCT Pub. No.: WO2006/081701
PCT Pub. Date: Aug. 10, 2006

(65) Prior Publication Data
US 2009/0029348 A1    Jan. 29, 2009

(51) Int. Cl.
*A61K 39/29* (2006.01)
*A61K 39/00* (2006.01)
*A61K 39/12* (2006.01)
*C12Q 1/00* (2006.01)
*G01N 33/53* (2006.01)

(52) U.S. Cl. .............. 424/189.1; 424/184.1; 424/192.1; 424/229.1; 435/4; 435/7.1; 435/7.9; 435/7.92

(58) Field of Classification Search .......... None
See application file for complete search history.

(56) References Cited

U.S. PATENT DOCUMENTS

| 5,861,264 | A * | 1/1999 | Elrod et al. ............. 435/7.24 |
| 6,096,319 | A | 8/2000 | Seidel et al. |
| 2003/0027214 | A1 * | 2/2003 | Kamb ..................... 435/7.1 |
| 2003/0108563 | A1 | 6/2003 | Bahl |
| 2003/0152965 | A1 | 8/2003 | Bahl |
| 2004/0096822 | A1 * | 5/2004 | Chien et al. ................ 435/5 |

FOREIGN PATENT DOCUMENTS

| CN | 1548958 | | 11/2004 |
| EP | 0 967 485 | | 12/1999 |
| EP | 1452601 | * | 9/2004 |
| JP | 3287069 | | 12/1991 |

OTHER PUBLICATIONS

Beckett et al., "A minimal peptide substrate in biotin holoenzyme synthetase-catalyzed biotinylation," Protein Science, vol. 8, pp. 921-929 (1999).*
Bowie et al.,"Deciphering the Message in Protein Sequences: Tolerance to Amino Acid Substitutions," Science, vol. 247 No. 4948 pp. 1306-1310 (Mar. 1990).*
Mateu et al., "A single amino acid substitution affects multiple overlapping epitopes in the major antigenic site of foot-and-mouth disease virus of serotype C," Journal of General Virology, vol. 71, pp. 629-637 (Mar. 1990).*
Osborne et al., "Riffkin et al., "A single amino-acid change between the antigenically different extracellular serine proteases V2 and B2 from Dichelobacter r, odosus," Gene, vol. 167, pp. 279-283 (1995). ," FEBS Letters, vol. 324 No. 3, pp. 253-257 (Jun. 1993).*
Riffkin et al., "A single amino-acid change between the antigenically different extracellular serine proteases V2 and B2 from Dichelobacter r, odosus," Gene, vol. 167, pp. 279-283 (1995).*
Schatz, "Use of peptide libraries to map the substrate specificity of a peptide-modifying enzyme: a 13 residue consensus peptide specifies biotinylation in *Escherichia coli*," Bio/Technology, vol. 11 No. 10, pp. 1138-1143 (Oct. 1993).*
Tsao et al., "A versatile plasmid expression vector for the production of biotinylated proteins by site-specific, enzymatic modification in *Escherichia coli*," Gene, vol. 169 No. 1, pp. 59-64 (Feb. 1996).*
International Search Report in PCT/CN2005/000149 dated Dec. 8, 2005.

\* cited by examiner

*Primary Examiner*—Zachariah Lucas
(74) *Attorney, Agent, or Firm*—Marshall, Gerstein & Borun LLP

(57) ABSTRACT

A kit and its preparing method concerning dual-antigen sandwich method are used for detecting the antibody against HCV, and its detecting mode is 'carrier-first antigen-antibody against HCV to be detected-second antigen-marker-distinguishable signal'. The kit ant its preparing method characterize in that the second antigen is the complex of a HCV and a tag.

1 Claim, 3 Drawing Sheets

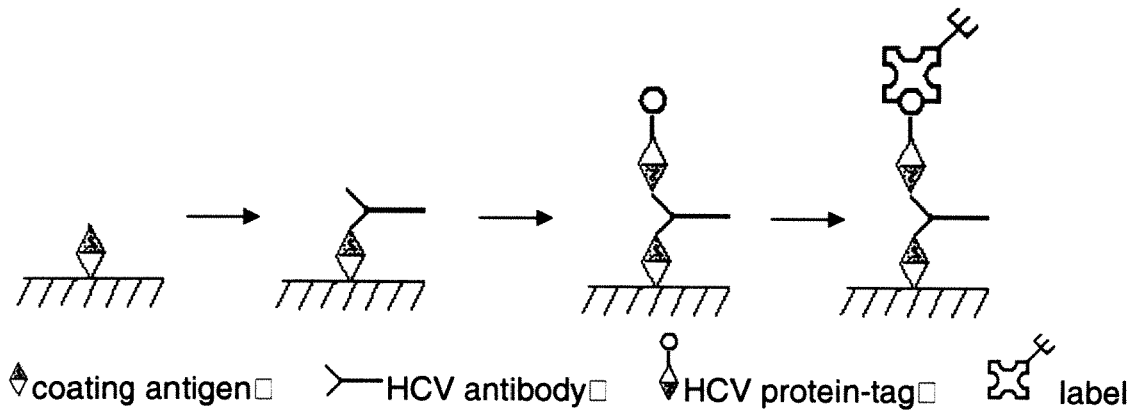
Figure 1. Schematic diagram of the detection method of direct recognition of the second antigen by label.
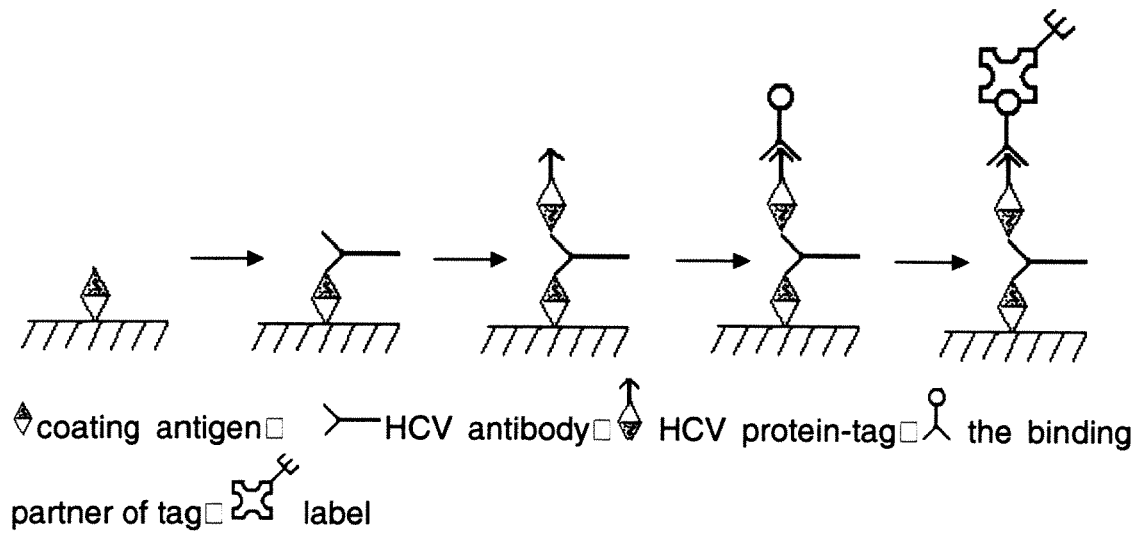
Figure 2. Schematic diagram of the detection method of indirect recognition of the second antigen by label.

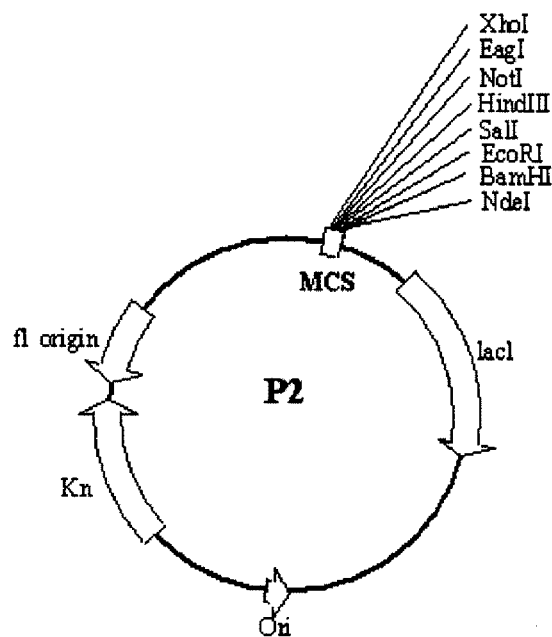
Figure 3. Plasmid profile of expression plasmid P2
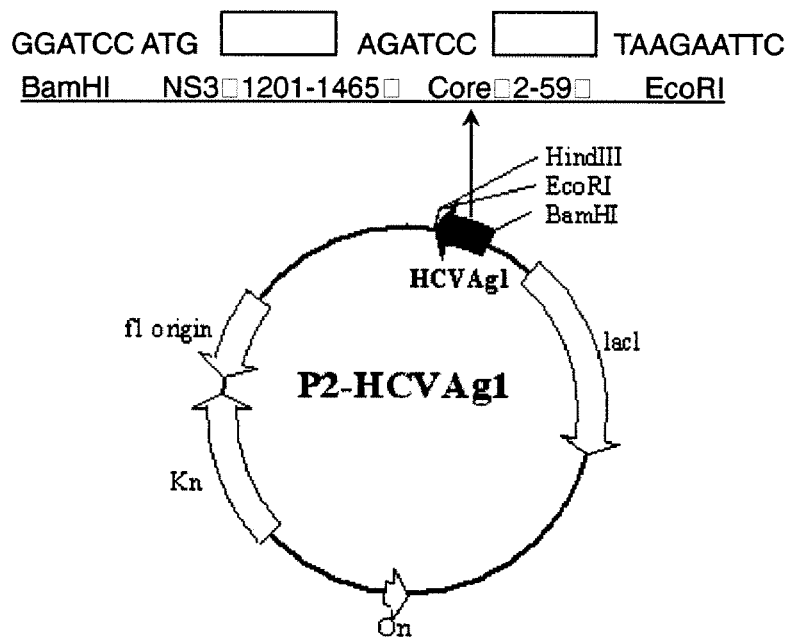
Figure 4. Plasmid profile of expression plasmid P2-HCVAg1 of the primary antigen

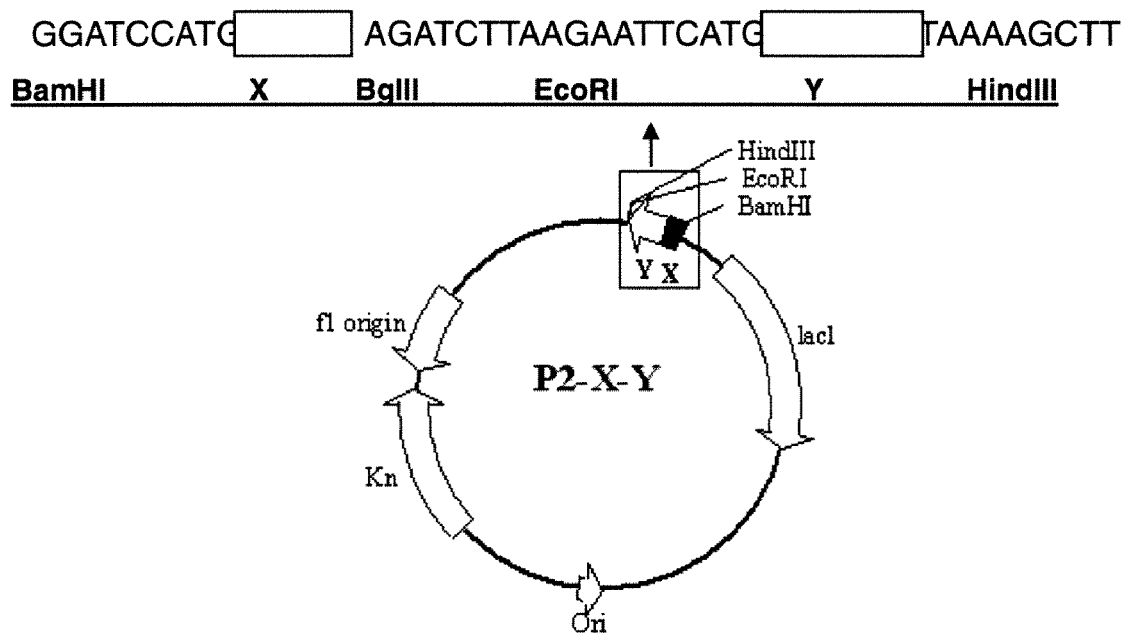
Figure 5. Plasmid profile of bi-cistron expression plasmid P2-X-Y of the second antigen

KIT FOR DETECTING THE ANTIBODY OF HCV AND ITS PREPARING METHOD

TECHNICAL FIELD

The present invention relates to immunodiagnosis, and in particular, to a kit for detecting an HCV antibody and a method for preparing the same.

BACKGROUND

Hepatitis C is a severe hepatic disease caused by hepatic C virus (HCV). About 170 million people have been infected with HCV all over the world and over 40 million have been infected in China. About 50~85% of the HCV-infected individuals will subsequently develop into chronic hepatitis and about 10~15% will develop into hepatocirrhosis. So HCV is of huge harm to human health and lays a heavy burden on our society.

HCV diagnosis has been developed greatly since Choo et al managed to clone the HCV gene in 1989. At present, there are three main approaches to detecting Hepatitis C: detecting the HCV RNA by polymerase chain reaction (PCR); detecting the HCV antigens using a monoclonal antibody; and detecting the HCV antibody with Enzyme Linked Immunosorbent Assay (ELISA) and Western blotting, etc.

The ELISA reagent for detecting an HCV antibody has developed into the third generation. The primary Elisa-1 kit was developed by Ortho Clinical Diagnostics Inc. (U.K.) in 1990, using the HCV NS4 recombinant antigen C100-3 provided by Chiron (USA). Unfortunately, the Elisa-1 kit has rather unsatisfactory sensitivity and specificity. Thereafter, the Elisa-2 kit took the place of the Elisa-1 kit. The Elisa-2 kit was developed by Ortho Clinical Diagnostics Inc. (U.K.) and Abbott (USA) respectively, using antigens such as CORE, NS3 and NS4. The Elisa-2 kit has its sensitivity and specificity improved. It is found that the positive rate is 92~95% when the Elisa-2 kit is applied to the chronic hepatitis C patients and the average window period of HCV seropositive conversion is shorted from 16 weeks to 10 weeks due to the application of CORE and NS3 antigens. Further, the Elisa-3 kit is developed and produced by Ortho Clinical Diagnostics Inc. (U.K.), Abbott (USA) and Sanofi (France) in the lead, using antigens such as CORE, NS3, NS4 and NS5. It is found that the sensitivity thereof is increased to about 97% and the average window period of HCV seropositive conversion is shorted to 7~8 weeks when the ELISA-3 kit is used to detect HCV in blood donors and high risk groups.

Elisa has such advantages that it can be easily automated, conveniently operated and well reproduced in diagnosis. Moreover, it is low in cost and helpful in analysis and storage of the experimental data. Nowadays, commercial reagents that are employed all over the world for screening the HCV antibody are mainly Elisa-2 and Elisa-3 kits developed with the indirect method. Despite the improvements for three generations, the Elisa reagents are still quite disadvantageous as shown by the false negative, false positive, and uncertain results that mainly arise from the inherent defects of the indirect reagents in methodology. Specifically, the disadvantages are as follows:

1. Poor specificity. The indirect method applies labels of non-specific recognition to the second antibody, which leads to low specificity.

2. Low sensitivity. Because of poor specificity, the concentrations of the coating antigens and the labeled second antibody in the kits have to be lowered, the amount of the specimens to be detected has to be reduced, and the specimens have to be diluted in duplication, which thereby lowers sensitivity.

3. Long window period. The common second antibody is the anti-IgG antibody that can only detect the IgG components in the antibody but cannot detect other types of antibody, especially the IgM antibody in the early period, which lowers sensitivity and prolongs the window period.

At present, 70% of the post-transfusion hepatitis cases are infected with Hepatitis C after blood transfusion, and 80☐90% of the Hepatitis C-infected individuals fall within the group of post-transfusion infection, which results to a large degree from the above-mentioned defects of the current indirect reagents. Therefore, there is a need to develop an HCV antibody diagnostic reagent of high sensitivity and high specificity.

Double-antigen sandwich method substitutes a labeled antigen for a labeled second antibody in the indirect method, thereby overcoming the defects of the indirect method methodologically. Although it is widely applied to antibody detection nowadays, the rather advanced double-antigen sandwich method is still not employed in the kit for screening of the HCV antibody for two main reasons:

1. The Activity Loss Following the Labeling of HCV Protein

Presently labeling the antigen directly with a label such as peroxidase horseradish (HRP) is the dominant enzyme labeling method, but some problems arise when this method is applied to the labeling of HCV antigen. Firstly, the NS3 antigen as a main antigen epitope segment of HCV, is an antigen strongly dependent on its conformation; when labeled by a "flexible" label with a high molecular weight such as peroxidase horseradish or alkaline phosphatase, it varies greatly in conformation, and its active epitopes are difficult to expose. As such, the activity of labeled NS3 antigen will be substantially decreased. Secondly, the main active region of CORE antigen as another main antigen epitope segment of HCV contains lots of Lysine which are critical to the activity of CORE, and the free amino-group in the side chain of Lysine is often used as the target for label reaction (such as labeling HRP by NaIO4 oxidization). Accordingly, the activity of CORE antigen is greatly decreased after labeling, and as a result the sensitivity of the kits produced is even poorer than that of indirect methods, which may leads to higher possibilities of mis-diagnosis.

2. The High Background

The CORE antigen has a strong homologous and heterogenous binding capacity in vitro or in vivo (Matsumoto, M. etc., Virology, 218:P 43-51, 1996; Kunkel, M. etc., Virology, 294: P 239-245, 2002; Majeau, N. etc., Journal of General Virology, 85: P 971-981, 2004)). In the double-antigen sandwich method, the labeled antigen (the secondary antigen) can bind homologously with the coated antigen (the primary antigen), which leads to high background of the kit.

By now there are lots of reports about the reagent for detecting the HCV antibody by the double-antigen sandwich method at home and abroad, but each is subjected to some defects mainly as follows:

The method introduced in the patent application of the publication No. CN 1548958A firstly took no account of the importance of the size of heterologous protein for maintaining activity of HCV antigen, particularly NS3 antigen, hence failed to screen the pontine protein, i.e., did not use the pontine protein having a molecular weight as small as possible to ensure the activity of HCV antigen so as to further ensure sensitivity of the kit. Secondly, the method did not add a certain proportion of sulfhydryl reagents (like β-mercaptoethanol or dithiothreitol, etc.) or denaturants (like sodium dodecyl sulfonate) (see U.S. Pat. No. 6,270,960 and U.S. Pat. No. 6,261,764 for more details) into a coating liquid or add a certain proportion of sulfhydryl reagents into a blocking liquid, which prevented the coating antigen from showing its activity completely, thereby lowering sensitivity of the kit. Thirdly, the method did not add a certain proportion of sulfhydryl reagents into the dilution liquid of the secondary antigen, which prevented the secondary antigen from showing its activity completely, thereby lowering sensitivity of the kit. Fourthly, the method failed to put forward a solution to the problem of high background caused by various binding tendencies of CORE antigens. In addition, in the examples of the patent application, the protein expressed by the empty vector pET-32a(+) contained His Tag, so that the polyclonal antibody labels thereof also included anti-His Tag antibody labels; however, since its coating antigen contained His Tag, the anti-His Tag antibody labels could combine directly with the coating antigen to develop color, so that all sera, either negative or positive, would present a positive reaction.

Although the method introduced by Baochang Lee et al (Journal of Experimental Hematology, 12(3): P 359-362, 2004) researched into HCV antigen biotinylation, the study was carried out merely on the level of antigen, without posing concrete solutions to the above-mentioned problem that might be confronted in the development of the HCV antibody diagnostic reagents of the double-antigen sandwich method. Moreover, the method proposed in the article for biotinylating HCV protein using primitive biotin-[acetyl-CoA carboxylase] synthetase of *Escherichia coli* in vivo had rather low efficiency in biotinylation, only 10% or so (Paul A. S. et al, Nucleic Acids Research, 26(6): P 1414-1420, 1998; Tsao, K. L. et al, Gene, 169: P59-64, 1996). To eliminate as much as possible the influence on sensitivity by competition of, when reacting as the secondary antigens, non-biotinylated antigens with biotinylated antigens, said biotinylation method had to separate the biotinylated antigens, which lowered the yield rate of biotinylated antigens and increased difficulty and cost of subsequent purification.

Although patent applications U.S. Pat. No. 6,096,319, U.S. Pat. No. 6,270,960 and U.S. Pat. No. 6,306,579 mentioned the HCV double-antigen bridge-sandwich method, they posed no substantive solution to the above-said difficulties. In fact, these patent appliations only set forth theories to apply various double-antigen sandwich diagnostic methods that were already rather mature in other fields to HCV diagnosis.

In the HCV double-antigen bridge-sandwich method disclosed in patent application U.S. Pat. No. 6,613,530, the antigens (including primary antigen and secondary antigen) were conjugates of HCV protein and carrier protein. Protein carriers (BSA, 69 KD; β-Gal, 465 KD; Bovine-Fab, 75 KD) with a larger molecular weight were only applicable to coupling short peptides of HCV, while the conformation-dependant HCV antigen, particularly NS3 segment antigen, had its activity obviously lowered when this method was employed, which thereby affected sensitivity of the kit.

The double-antigen sandwich method involved in the article of Cheng Cao et al (Chinese Journal of Medical Laboratory Technology, 19(4): P 205-207, 1996) was just an initial attempt to transplant double-antigen sandwich diagnostic methods that were already rather mature in application to other fields directly into HCV diagnosis, labeling HRP directly onto free lysine of unengineered HCV protein without considering the above characteristics of HCV protein, which greatly reduced activity of the labeled antigens, whereby the kits had the severe disadvantage of false negative results.

Using a kit for detecting an HCV antibody developed with the double-antigen sandwich method, this invention can not only fundamentally overcome the diverse disadvantages of the indirect method from the methodological perspective, but also solve the technical problems existing in the present double-antigen sandwich kit. That is, the present invention managed to develop a kit for detecting an HCV antibody applicable to clinical settings, which provides a more favorable tool for screening HCV.

OBJECTIVES OF THE INVENTION

The objective of the present invention is to solve the problem of high background caused by the CORE antigen in the HCV kits of the double-antigen sandwich method and to solve the problem of loss of activity after the labeling of HCV protein, so as to further combine a biotin-avidin magnifying system to provide a new kit for detecting the HCV antibody by the double-antigen sandwich method with its sensitivity and specificity much improved over the present commercial reagents.

SUMMARY OF THE INVENTION

The present invention provides a kit for detecting an HCV antibody, said kit completing detection in a form of 'a support-a primary antigen-an HCV antibody to be detected-a secondary antigen-a label-a recognizable signal', wherein the secondary antigen undergoes a combination reaction with the label in one or more steps, characterized in that the secondary antigen is a conjugate of HCV protein and tag.

In an embodiment of the present invention, said tag is peptide tag or non-peptide tag.

In a further embodiment of the present invention, said non-peptide tag is compound, half antigen, vitamin, steroid, dye, hormone, antibiotic, nucleic acid or any combination thereof with peptide or protein.

In a preferred embodiment of the present invention, the compound is dinitrophenol or bromodeoxyuridine; the vitamin is biotin or its derivatives; the steroid is digoxin; and the dye is acridine ester, rhodamine, dansyl chloride, fluorescein, Oregon Green, Lucifer yellow, Alexa Fluor, or Cascade Blue.

In a further preferred embodiment of the present invention, said non-peptide tag is biotin or its derivatives, or any combination of biotin or its derivatives with peptide or protein.

In a further embodiment of the present invention, the peptide tag is a peptide or protein containing His Tag, T7 Tag, S Tag, Flag Tag, HA Tag or an HCV peptide fragment.

In the preferred embodiments of the present invention, when the peptide tag is heterologous protein, its molecular weight is less than 30 KD, preferably less than 20 KD, further preferably less than 15 KD, still further preferably less than 10 KD, and even further preferably less than 5 KD.

In a preferred embodiment of the present invention, when the heterologous protein is at N-terminal of HCV protein, its molecular weight is less than 5 KD; and when the heterologous protein is at C-terminal of HCV protein, its molecular weight is less than 20 KD.

In an embodiment of the present invention, the primary antigen and the secondary antigen include HCV NS3 and CORE protein segment, wherein said NS3 protein segment is any segment starting from a.a.1201±5 and ending at a.a.1465±8 and has mutation(s) while keeping its antigenicity unchanged; and said CORE protein segment is a segment containing a.a.10-17 complete sequence, further a segment containing a.a.7-21 complete sequence, still further a segment containing a.a.6-23 complete sequence, and excluding a.a.29-90 complete sequence, further excluding a.a.29-70 complete sequence, still further excluding a.a.29-59 complete sequence, and even further excluding a.a.32-48 complete sequence, and has mutation(s) while keeping its antigenicity and binding ability unchanged.

In a preferred embodiment of the present invention, the CORE protein segment of the primary antigen is a.a.2-59; the CORE protein segment of the secondary antigen is a.a.1-28; and NS3 protein segments of both the primary antigen and the secondary antigen are a.a.1201-1465.

In an embodiment of the present invention, the binding partner of said tag is an anti-tag antibody or a receptor of said tag.

In a further embodiment of the present invention, when the tag is selected from biotin or its derivatives, or the combinations of biotin or its derivatives with peptide or protein, its binding partner is avidin, streptomycin, neural chain avidin and their analogs, antibodies raised against biotin or its derivatives; and when the peptide tag is used, its binding partner is a monoclonal or polyclonal antibody of the peptide or protein.

The present invention also provides a method for preparing said kit, which comprises steps of binding HCV protein and tag, said binding method including:

1. Biotinylation of HCV protein: including enzymatic biotinylation in vivo, biotinylation in vitro, indirect biotinylation, and biotinylation of amino acid; and 2. Chimeric expression of HCV protein and peptide.

In a further embodiment of the present invention, the method of enzymatic biotinylation in vivo is to co-express chimeric gene (shortened as "X") encoding HCV protein and biotin acceptor protein with gene (shortened as "Y") encoding biotin-[acetyl-CoA carboxylase] synthetase in a host in vivo, and bind particular lysine residues of the protein encoded by the chimeric gene X with biotin via enzymatic reaction in vivo with the expressed biotin-[acetyl-CoA carboxylase] synthetase in the host to prepare biotinylated HCV protein, wherein said co-expression includes:

1) polycistron expression;
2) co-transformation expression;
3) polypromoter expression;
4) monocistron expression; and
5) co-expression with biotin-[acetyl-CoA carboxylase] synthetase gene in the host.

In another embodiment of the present invention, the biotinylation in vitro is to biotinylate the HCV protein by coupling activated biotin or enzymatic reaction in vitro.

In an embodiment of the present invention, the biotin acceptor protein is a member of biotin carboxyl-carrier protein family or functional segments thereof, polypeptide as set out in SEQ ID NO. 3 or its functional analogs.

In an embodiment of the present invention, the Biotin-[acetyl-CoA-carboxylase] synthetase is enzyme classified as EC6.3.4.15 or functional segments and functional analogs thereof.

DESCRIPTION OF THE FIGURES

FIG. 1 is a schematic diagram depicting the detecting method of direct recognition of the secondary antigen by label.

FIG. 2 is a schematic diagram depicting detection method of indirect recognition of the second antigen by label.

FIG. 3 is a plasmid profile depicting expression vector P2. (SEQ ID NO: 14)

FIG. 4 is a plasmid profile depicting expression plasmid P2-HCVAg1 of primary antigen. (SEQ ID NO: 15)

FIG. 5 is a plasmid profile depicting bi-cistron expression plasmid P2-X-Y of expression secondary antigen. (SEQ ID NO: 16)

CONTENTS OF THE INVENTION

Definitions

The terms used herein are defined as follows unless specified otherwise.

The term 'primary antigen' used herein refers to the coating antigen in the present invention.

The term 'secondary antigen' used herein refers to a conjugate of HCV protein and tag in the present invention. The secondary antigen can be one or more, and respective tags thereof shall satisfy the conditions set in the present invention.

The term 'label' used herein refers to the agents that are labeled with detectable agents, wherein said detectable agents include, but are not limited to, enzymes, such as horseradish peroxidase, alkaline phosphatase, β-galactosidase; chemical illuminants, such as acridinium ester; fluorescence agents such as fluorescein isothiocyanate, europium, europium nanometer particles and so on; radioactive agents, such as $^{125}$I and so on; and colloids, such as colloidal gold, latex and so on. The detectable agents can also be combinations of one or more of the above-mentioned agents.

The term 'heterologous protein' used herein refers to peptide or protein moiety which is other than HCV-encoded protein and is in chimeric expression with HCV protein.

The term 'biotin or derivatives thereof' used herein refers to biotin or its functional derivatives, including but not limited to D-biotin, activated biotin, biocytin, ethylendiamine biotin, cadaverine biotin, desthiobiotin and so on, with the common characteristics of containing imidazolone rings which can bind with avidin or its functional analogs.

The terms 'peptide' and 'protein' used herein have the general meanings that persons of ordinary skills in the art will understand, and can be used interchangeably.

The terms 'CORE' and 'NS3' used herein refer to HCV core protein and non-structural protein 3 respectively. The former represents the a.a.1-191 segment of protein encoded by the whole HCV genes (where "a.a." is the abbreviation for amino acid, and in the present invention a.a.A-B represents a segment from amino acid No. A to amino acid No. B in the protein encoded by the whole HCV genes, wherein B>A), while the latter represents the a.a.1027-1657 segment of protein encoded by the whole HCV genes.

The term 'biotin acceptor protein' used herein refers to the biotin carboxyl-carrier protein (BCCP) family or the functional segments thereof, and SEQ ID NO. 3 polypeptide or the functional analogs thereof (see Peter, J. S. et al., Biotechnology, 11: 1138-1143, 1993). The biotin acceptor protein to be used in the present invention can be one or more of the above-mentioned peptides or proteins, or combinations thereof.

The term 'Biotin-[acetyl-CoA-carboxylase] synthetase' used herein comprises enzyme classified as EC6.3.4.15 or the functional segments and functional analogs thereof.

The term 'binding partner' used herein refers to a ligand or a receptor which can bind with a tag. When a non-peptide tag is selected, the binding partner thereof is a specific receptor or antibody of the tag. For example, if biotins or derivatives thereof or their combinations with peptide or protein, their binding partners are avidin, streptavidin, neural chain streptavidin and analogs thereof, and antibodies against biotin or its derivatives. When a peptide tag is selected, its binding partner is a monoclonal antibody or polyclonal antibody against the peptide or protein.

The term 'high background' used herein means that a detected OD value of an HCV negative specimen exceeds the normal background range of the kit according to the present invention, even reaching an OD value of a strong positive specimen in normal conditions.

The terms 'flexibility' and 'rigidity' used herein mainly refer to the structural lability of an agent. For example, when a macro molecule protein such as HRP etc. is cross-linked with an HCV antigen, the protein will "kink" with the HCV antigen, thereby changing the structure of the latter, and further affecting its activity. Such an agent is a 'flexible' agent. Inversely, when polystyrol, gold colloid, etc. are cross-linked with the HCV antigen, they will not "kink" together, in which case the HCV antigen has little change in conformation. Such an agent is a 'rigid' agent.

The term 'expression host' used herein comprises prokaryotic and eukaryotic expression system hosts, including but not limited to bacteria, such as *Escherichia coli, Bacillus subtilis* and so on; yeast such as *Pichia methanolica, Saccharomyces cerevisiae* and so on; eukaryotic cell such as entomic cell, mammalian cell and so on; virus; and tissue, organ or bio-reactor in vivo and so on.

The term 'support' used herein includes but is not limited to ELISA plate, bead, microparticle, slide, chip, plastics, membrane, etc. prepared by materials such as polystyrene, polyethylene, cellulose, nitrocellulose, acetylcellulose, silicide and so on.

The term 'sample/specimen to be detected' used herein refers to the body fluid from any species that may be infected with HCV, including but not limited to whole blood, serum, plasma, secretion, urine, saliva, cerebrospinal fluid, lymph fluid, tissue fluid, diachorema leachate, cell culture fluid or cell, tissue, organ homogenate and so on.

TAG

The term 'tag' used herein is an agent which can link with HCV protein and specifically bind to a binding partner to elicit subsequent detection reaction processes, including peptide tag and non-peptide tag.

Said peptide tag is peptide or protein, including peptide or protein containing His Tag, T7 Tag, S Tag, Flag Tag, HA Tag (many peptides can be selected, as detailed in the product introduction in the section of epitope tags by Abcam Inc.; http://www.abcam.com) or HCV peptide segments, which HCV peptide segments are not present in the primary antigen and do not have a binding capacity enough to cause high background, whose corresponding binding partner exists or can be prepared, characterized mainly in that the core substance which 'can specifically bind to a binding partner to elicit subsequent detection reaction processes' is peptide or protein. Said His Tag refers to six successive His, i.e., 6×His.

When said peptide tag is heterologous protein, its molecular weight is smaller than 30 KD, preferably smaller than 20 KD, more preferably smaller than 15 KD, still more preferably smaller than 10 KD, and even more preferably smaller than 5 KD.

When said heterologous protein tag of peptide kind is at N-terminal of HCV protein, it has a molecular weight smaller than 5 KD; and when at C-terminal, it has a molecular weight smaller than 20 KD.

Said non-peptide tag comprises compound (such as dinitrophenol, bromodeoxyuridine), hapten, vitamin (such as biotin or derivatives thereof), steroid (such as digoxin), dye (such as acridinium ester, rhodamine, dansyl chloride, fluorescein, Oregon Green, Lucifer yellow, Alexa Fluor, Cascade Blue), hormone, antibiotic, nucleic acid and so on (many non-peptides can be selected, as detailed in the product introduction to molecular probes by Invitrogen Corporation; http://www.probes.com), whose corresponding binding partner exists or can be prepared, characterized mainly in that the core substance which can specifically bind to a binding partner to elicit subsequent detection reaction process is non-peptide or non-protein.

Tags can be one or more tags or a combination of two or more tags, and can exist at N-terminal, C-terminal, both terminals of the HCV antigen or inside the HCV antigen.

Tag should be as small as possible so as to reduce its effect on HCV antigen activity.

Preparation and Detection Principles of the Kit of the Present Invention

The present kit accomplishes detection in the form of 'a support-a primary antigen-an HCV antibody to be detected-a secondary antigen-a label-a recognizable signal', wherein the secondary antigen undergoes one- or more-step association reactions with the label. The preparation and detection processes are mainly as follows:

Coating: coating the primary antigen onto the support.

Blocking: blocking the vacant sites on the support that are not coated by the primary antigen with inert protein, to avoid nonspecific absorption in the following reactions.

Primary antigen capturing antibody: adding the specimen to be detected before incubation to allow the primary antigen to capture the HCV antibody in the specimen.

Antibody capturing secondary antigen: adding the secondary antigen before incubation to allow the HCV antibody to capture the secondary antigen.

Detection: using a tag to introduce the label by one- or more-step incubation for detection.

The present kit is advantageous mainly in the following respects:

1. Achieving high activity labeling of HCV protein. In view of the loss of activity after the labeling of HCV protein, HCV protein is labeled indirectly using the particularly preferable method of biotinylating HCV protein or chimeric-expressing HCV protein with a peptide tag. Since the biotin or peptide tag has a rather small molecular weight, indirect labeling has little influence on the spatial structure of the antigen. Furthermore, by biotinylation of enzymatic reaction, the biotin can be site-directedly attached to particular lysine residues of the biotin acceptor protein which is chimeric with HCV protein. Through chimeric expression with HCV protein, the peptide tag can also be directedly inserted in a certain location of HCV protein, thereby better preserving activity of the HCV secondary antigen.

2. Solving the problem of high background of the HCV antibody diagnostic reagent in the double-antigen sandwich method. In view of the above-mentioned binding characteristics of the CORE antigen, the segments with high activity and weak nonspecific binding ability in the CORE antigen are screened out, thereby solving the problem of high background.

3. Biotin-avidin magnifying system raising sensitivity.

There is very strong affinity between avidin and biotin. Their binding affinity constant (Ka$\approx 10^{15}$ mol$^{-1}$) is at least 10 thousand times higher than the affinity constant (Ka$\approx 10^{5-11}$ mol$^{-1}$) of antigen and antibody. So the two agents can combine quickly without being interfered from outside. This system is a highly efficient biological response magnifying system applied to immunology in late 1970s. The preferred method for preparing the present kit is to label strepto-avidin with horseradish peroxidase and recognize the biotinylated HCV secondary antigen with the labeled, i.e., to utilize the biotin-avidin magnifying system as a bridge to achieve recognizing the secondary antigen indirectly by a label. Introduction of the system highly enhances sensitivity of the kit.

4. Three-step specific recognition raising specificity. In the present invention, the three steps of reactions in the process of detection are all specific recognition reactions: specific recognition of the primary antigen by the HCV antibody in the specimen; specific recognition of the HCV antibody by the secondary antigen; and specific recognition of the secondary antigen by the label. As seen, specificity of the reagent in the present invention is obviously improved over the traditional two-step specific recognition of the double-antigen sandwich reagent, and tremendously improved over the only one-step specific recognition of the indirect reagent.

Moreover, the detection principles of the present invention have a broad range of application, i.e., applicable to several immunoassay methods such as enzyme linked immunoassay, luminescence immunoassay, fluoroimmunoassay, radio-immunassay, microparticle immunoassay or immunogold assay, etc.

Preferred HCV Protein Segments in Primary Antigen and Secondary Antigen

The HCV gene used in the present invention is of the genotype of HCV 1b. Persons skilled in the art can infer from the conventional knowledge of the art that different genotypes of segments or combination of two or more genotypes of segments can be utilized in accordance with the genotype distribution in different areas while the selected amino segments remain the same.

In HCV protein, CORE and NS3 are the main HCV epitope segments. The epitope regions of CORE and NS3 are concentrated at N-terminal and C-terminal respectively, i.e. a.a.1-90 of CORE and a.a.1192-1657 of NS3. After analysis and screening of the above-mentioned segments, it is confirmed that the core epitope segments therein are a.a.7-21, 29-48 and 49-90 of CORE and a.a.1359-1454 of NS3. Through screening, we finally select a.a.1201-1465 (shortened as "G" hereinafter) as the NS3 segment antigen.

In addition, it is found upon research that the main segment that leads CORE protein to bind is a.a.1-90. To solve the problem of high background caused by the CORE antigen in the kit for detecting an HCV antibody by the double-antigen sandwich method, we design a number of chimeric-expressed antigens of different CORE segments and NS3 G segments as the primary antigens and the secondary antigens respectively, so as to screen out a gene segment scope of the CORE antigen which can both keep high sensitivity of the CORE antigen and ensure that its binding ability will not affect the development of the kit for detecting an HCV antibody by the double-antigen sandwich method. It is concluded that the CORE segments in the HCV antigen of the double-antigen sandwich method are supposed to measure up to the characteristics of: a segment containing a.a.10-17 complete sequence, further a segment containing a.a.7-21 complete sequence, still further a segment containing a.a.6-23 complete sequence, and excluding a.a.29-90 complete sequence, further excluding a.a.29-70 complete sequence, still further excluding a.a.29-59 complete sequence, and even further excluding a.a.32-48 complete sequence. Said protein segment can have mutation(s) while keeping its antigenicity and binding ability unchanged.

The above conditions are important for developing the kit of the present invention and other detection kits for the HCV double-antigen sandwich method using antigens containing the CORE segment.

At last, we determine the CORE segment of the primary antigen as a.a.2-59 and the CORE segment of the secondary antigen as a.a.1-28.

Combination of HCV Protein with Tag in Secondary Antigen

The present invention introduces tag and its binding partner to complete labeling HCV protein indirectly. An important criterion for choosing tag is that the tag shall be as small as possible to reduce damage to activity of the HCV antigen. Tag can be one or more tags or combination of two or more tags, and can bind at N-terminal, C-terminal or both terminals of HCV protein or inside HCV protein.

All non-peptide agents that have or can be prepared with their corresponding binding partners, such as compound (dinitrophenol or bromodeoxyuridine), vitamin (biotin or derivatives thereof), steroid (digoxin), dyestuff (acridinium ester, rhodamine, dansyl chloride, fluorescein, Oregon Green, Lucifer yellow, Alexa Fluor, Cascade Blue) and so on, or their combinations with peptide or protein can be the tag of the present invention.

All peptides or proteins, e.g., peptides like His Tag, etc. which have or can be prepared with their corresponding binding partners can also be the tag of the present invention.

Some detectable chemoluminescence agents of small molecule (such as acridinium ester), fluorescent agents (such as fluorescein isothiocyanate, europium), radioactive isotopes (such as $^{125}$I) etc., or detectable agents of 'rigid' macromolecule such as gold colloids, latex particles, nanometer particles coupled with labels etc. can label HCV protein directly into a labeled antigen for use in double-antigen sandwich detection. These detectable agents can be regarded as special tags of the present invention to some extent.

As for selection of the tag, persons skilled in the art can make inference from the existing experimental methods on the basis of the above principles. Accordingly, no more details will be provided. Here we just take His Tag to represent peptide tags and biotin or derivatives thereof to represent non-peptide tags for illustration.

The preferred method for binding HCV protein with tag of the present invention is to biotinylate HCV protein and to chimeric-express HCV protein with peptide.

1. Biotinylation of HCV Protein

The specific methods for biotinylating HCV protein include:

a) enzymatic biotinylation in vivo;

b) biotinylation in vitro;

c) indirect biotinylation; and d) biotinylation of amino acid.

1.1 Enzymatic Biotinylation In Vivo

The present invention generally co-expresses chimeric gene X encoding biotin acceptor protein and HCV protein with gene Y encoding biotin-[acetyl-CoA carboxylase] synthetase in a host in vivo, and binds particular lysine residues of the protein encoded by the chimeric gene X with biotin via enzymatic reaction in vivo with biotin-[acetyl-CoA carboxylase] synthetase in the expression host in vivo to prepare biotinylated HCV protein.

Natural biotin acceptor protein mainly exists in the biotin carboxyl carrier protein family, whose core is the protein or peptide containing lysine of special sites that binds to biotin. Polypeptide as set out in SEQ ID NO. 3 is synthesized, which has the same ability to bind biotin as biotin carboxyl carrier protein. The two kinds of biotin acceptor proteins are common in binding with biotin under the effect of biotin-[acetyl-CoA carboxylase] synthetase, and can both be used in this detection system. We take the gene encoding products of SEQ ID NO. 3 as the biotin acceptor protein for illustrating the present invention.

Biotin-[acetyl-CoA carboxylase] synthetase which can catalyse biotinylattion of protein roots in various sources, including but not limited to bacteria, such as *Escherichia coli, Bacillus subtilis, Haemophilus influenzae, Rhizobium, Lactobacillus, Salmonella typhimurium, Synechocystis* sp., *streptococcus* and Paracoccusdenitrificane BirA gene encoding products; *Rickettsia mooseri* BirA gene encoding products; *Methanococcus jannaschii* MJ1619 gene encoding products; *Treponema Pallidum* TP0357 gene encoding products; yeasts, such as *Schizosaccharomyces pombe* SPBC30D10.07c gene encoding products and *Saccharomyces cerevisiae* BPL1 gene encoding products; plants, such as *Arabidopsis thaliana* BirA gene encoding products; and animals, such as *Homo sapiens* or *Mus musculus* HLCS gene encoding products, etc. Biotin-[acetyl-CoA carboxylase] synthetase also includes the functional segments or functional analogs of the above above enzymes. We take BirA gene products of *Escherichia coli* ER2566 for illustrating the present invention.

1.1.1 Polycistron Expression

Polycistron expression is a method for expressing genes X and Y in the form of polycistron in the host under the effect of the same promoter in the expression vector so as to accomplish the biotinylation.

Operon is an important form of prokaryotic gene expression regulation. Most *Escherichia coli* genes constitute gene expression regulatory units in the form of operons. Regulated genes encoding proteins in operons are structural genes. One operon has more than two structural genes, even up to more than ten. Every structural gene is a successive open reading frame, which has a translation initiation code at 5'-terminal and a translation termination code at 3'-terminal. All structural genes are connected with each other end to end, and arranged in tandem to form structural gene groups. There is a ribosome binding site at least at 5'-side of the first structural gene. Therefore, when this DNA segment which contains two or more structural genes is transcribed to a polycistronic mRNA, it can be recognized by and bound to ribosome to start translation. Ribosome moves along the mRNA. After synthesizing the first encoded polypeptide, the ribosome can continue to translate and synthesize the next gene-encoded polypeptide without departing from the mRNA until it has completed synthesizing all polypeptides encoded by the polycistronic mRNA.

The above-mentioned form of polycistron expression exists in many biosystems. According to the above principles, we may ligate X and Y into an expression vector in the form of a bi-cistronic, which, after shifted into the expression host, attach the biotin that has been added into the culture medium to the particular lysine sites of biotin acceptor protein in chimeric expression with HCV protein utilizing the agents and environment in a host in vivo and biotin-[acetyl-CoA carboxylase] synthetase expressed by Y, and thus accomplish biotinylating HCV protein site-directedly.

The polycistrons here may have X at N-terminal or C-terminal, and may be polycistrons arranged and combined in all forms like one X and several Y, one Y and several X, or several X and several Y, and so on.

In all the methods for biotinylating antigen in the present invention, the 'Polycistron expression' is the steadiest, the most convenient, and of the lowest cost, and thereby is taken as the preferred method for biotinylating antigen and binding HCV protein to tag in the present invention.

1.1.2 Co-Transformation Expression

Co-transformation expression is a method for transforming two different expression vectors into which gene X and gene Y have been cloned respectively into the expression host together for co-expression so as to accomplish the biotinylation.

Since gene X and gene Y are cloned into two different expression vectors respectively, the two expression vectors may have either identical or different properties, as long as they can express HCV antigen with chimeric biotin acceptor protein and biotin-[acetyl-CoA carboxylase] synthetase respectively under the corresponding resistance selection pressure, and ensure that biotin-[acetyl-CoA carboxylase] synthetase can biotinylate HCV antigen to the maximum extent.

1.1.3 Poly-Promotor Expression

Poly-promotor expression is a method for initiating and transcribing genes X and Y using different promoters in the same expression vector respectively for co-expression in the expression host so as to accomplish the biotinylation.

Gene X and gene Y were cloned down stream of two promoters respectively regulated by different operons of the same expression vector for effective transcription and translation, so as to achieve co-expression of HCV antigen with chimeric biotin acceptor protein and biotin-[acetyl-CoA carboxylase] synthetase in the same host and accomplish biotinylating HCV antigen.

1.1.4 Monocistronic Expression

Monocistronic expression is a method for chimeric-expressing gene X and gene Y in the form of monocistron in different ways so as to accomplish biotinylation.

Gene X and Y may be chimeric-expressed in different forms. The expressed chimeric proteins have not only the function of synthetase but also the acceptability of biotin, which allows mutual biotinylation among chimeric proteins. Said different ways here may be X at N-terminal or C-terminal, or may be all forms of arrangement and combination like one X and several Y, one Y and several X, or several X and several Y, and so on.

1.1.5 Co-Expression with Biotin-[Acetyl-CoA Carboxylase] Synthetase Gene of a Host Co-expression with biotin-[acetyl-CoA carboxylase] synthetase gene of the host is a method for biotinylating protein encoded by gene X to the maximum extent using biotin-[acetyl-CoA carboxylase] synthetase expressed by genes with similar functions to gene Y in the expression host.

By employing the gene engineering method, we may integrate endogenous or heterologous genes encoding biotin-[acetyl-CoA carboxylase] synthetase into the expression host, or activate primordial genes similar to biotin-[acetyl-CoA carboxylase] synthetase gene in the expression host in a certain manner to increase the expression level thereof, so that the expressed biotin-[acetyl-CoA carboxylase] synthetase biotinylates the fusion protein of HCV protein and biotin acceptor protein to the maximum extent. Alternatively, we may use biotin-[acetyl-CoA carboxylase] synthetase expressed by the endogenous genes of the expression host with similar functions to gene Y to partly biotinylate HCV protein. Generally, the expression level of the host endogenous genes with similar functions to Y is rather low, so that the unengineered original host can just biotinylate protein or peptide bindable to biotin in vivo at low efficiency. Therefore, the latter method needs to remove most non-biotinylated antigens while purifying the antigens, so as to eliminate as much as possible the competition of the non-biotinylated antigens when used as the secondary antigens to the biotinylated antigens. It is preferred that other biotinylation methods also remove the non-biotinylated antigens to increase sensitivity.

1.2 Biotinylation In Vitro 1.2.1 Labeling HCV Protein with Activated Biotin

Activated biotin is directly coupled to HCV protein through the coupling method. Please refer to the catalogue of PIERCE Inc. (USA) as concerns the HCV protein groups to be coupled to, and the specific methods for selectiong and coupling the activated biotin.

1.2.2 Adding Biotin onto HCV Protein by Enzymatic Reaction In Vitro

Enzymatic reaction in vitro generally means mixing the products encoded by gene X with biotin-[acetyl-CoA carboxylase] synthetase in vitro and providing an appropriate environment for enzymatic reaction, so that biotin-[acetyl-CoA carboxylase] synthetase can biotinylate HCV protein by enzymatic reaction in vitro.

1.3 Indirect Biotinylation

Indirect biotinylation means linking HCV protein with agent A, binding agent A with agent B, then binding agent B with agent C, where the rest may be deduced by analogy, thereby achieving one- or more-stage recognition of A; and linking biotin onto the binding agent at the last stage with the above-mentioned biotinylation method to finally achieve biotinylating HCV protein indirectly in the form of HCV protein-A(-B-C . . . )-biotin.

1.4 Biotinylation of Amino Acid

Biotinylation of amino acid is to biotinylate one or several certain amino acids (Shen et al, Synthetic Chemistry, 10(4): 359-361, 2002) as the host culture medium components to be added into the expression system, and to incorporate biotin into the peptide chains of HCV protein by the protein translation process of the host so as to prepare the biotinylated secondary antigen.

2. Chimeric Expression of HCV Protein and Peptide

Besides biotin tags, peptide agents may also be used as tag of the secondary antigen. Peptide tags can be incorporated at N-terminal, C-terminal, both terminals of the HCV antigen or inside the HCV antigen using the method of genetic engineering chimeric expression. In such event, the binding partner of the tag is a specific recognition agent of the peptide agents, such as a monoclonal antibody or a polyclonal antibody.

HCV antigen has certain particularities as shown in its activity that decreases with the increase in the molecular weight of heterologous protein, which appears more marked in fusion at N-terminal. In this regard, the present invention selects peptide with a molecular weight as small as possible to be the tag.

The peptide tags that may be used in the present invention comprise His Tag.

2.1 Non-HCV Peptide Tag

The non-HCV peptide tag to be selected herein comprises His Tag. In accordance with the genetic engineering method, the gene encoding His Tag and the gene coding HCV protein are chimeric-expressed to prepare the secondary antigen, and a labeled anti-His Tag monoclonal antibody is used to recognize the secondary antigen, thereby finishing detection.

2.2 HCV Peptide Tag

The following have to be noted in selection of HCV peptide as the tag:

1) The HCV peptide fragment should be a segment whose antibody has no specific affinity with the primary antigen so as to prevent the label from binding with the primary antigen; and 2) It is preferred that the HCV peptide fragment avoid the HCV protein segment with intense binding tendency so as to avoid high background of the kit.

The specific preparation and detection processes thereof are similar to those mentioned above.

The following examples are provided for further illustration of this invention.

Example 1

Preparation of Primary Antigen

The present invention obtained the engineered vector pTO-T7 referring to method of Wenxin Luo et al, Chinese Journal of Biotechnology, 16(5): P 578-581, 2000. We synthesized primers to amplify the gene sequence between NdeI and BamHI sites, wherein the upstream primer had NdeI and BamHI sites, and the downstream primer had BamHI and EcoRI sites. After recovery (all molecular biology extraction and purification kits used were bought from Watson Biotechnologies, Inc., Shang Hai, China), the fragment was cleaved by restriction endonuclease NdeI/EcoRI (all kinds of molecular biology enzymes used were bought from TAKARA Biotechnology Co., Ltd., Dalian, China) and cloned into the pTO-T7 vector cleaved by the same endonuclease. Positive clone was cleaved by one single restriction endonuclease BamHI, then recovered and self-ligated (i.e., to remove T7 Tag gene between NdeI and BamHI sites in pTO-T7 vector). The vector thus obtained was named P1.

Upstream of the T7 promoter of P1 vector there was one BglII site, which is disadvantageous to cloning of the present invention. As such, primers were synthesized to amplify the segments between BglII and XbaI sites of P1 vector, such that upstream primer had BamHI site and downstream primer had XbaI site. The segment was cleaved by BamHI/XbaI and then cloned onto P1 vector cleaved by restriction endonuclease BglII/XbaI. Therefore, the positive clone obtained was expression plasmid P2 in which BglII site was blocked, and was also the clone vector used in the present invention. In practicing the present invention, P1 and P2 were not the necessary expression vectors, the upstream enhancer thereof also had no substantive function in the present invention, and construction of these vectors were just for the convenience of cloning. Many other expression vectors such as pET-24a(+) (Novagen, USA, Article No. 69749-3) could also be used in the present invention practice.

We amplified a.a.1201-1465 gene by PCR; the upstream primer thereof had BamHI site, and the downstream primer had BglII and EcoRI sites and a termination codon TAA therebetween. Then, we amplified a.a.2-59 gene by PCR; the upstream primer thereof had BamHI site, and the downstream primer had EcoRI site. By cloning the segment of a.a.1201-1465 cleaved by BamHI/EcoRI endonucleases into expression vector P2 cleaved by the same endonucleases, we got the plasmid P2-G. By Inserting a.a.2-59 gene cleaved by BamHI/EcoRI into said expression vector cleaved by the BglII/EcoRI endonucleases, we obtained the positive clone P2-G-CORE (a.a.2-59) which was also the expression plasmid of the primary antigen of this invention and named P2-HCVAg1. The ER2566 strain containing the plasmid (*Escherichia coli* ER2566/P2-HCVAg1) had been stored in China Center for Type Culture Collection (Wuhan University, Luojia hill, Wuchang district, Wuhan, Hubei province, China) in Jan. 21, 2005, with the access number of CCTCC M 205009, and the antigen expressed by this plasmid was named HCVAg1. The present invention applied the same method to construct the clone designed while screening the first antigen.

P2-HCVAg1 was transformed into *Escherichia coli* ER2566 (New England Biolabs, Inc., USA), which was spread on LB plate containing 100 ug/ml Kanamycin (Shanghai Sangon Biological Engineering Technology&Services Co., Ltd., "Sangon" for short, Article No. KE170) and cultured at 37° C. overnight. Then monocolone was selected and placed in a bottle of 500 ml LB liquid culture medium which contained the same concentration of Kanamycin to shake culture it to OD600 1.0 approximately. Thereafter IPTG (Sangon, Article No. IB0168) whose final concentration was 0.5 mM was added to induce, at 37° C., 200 rpm for 4 hours. Induced cells were centrifugated at 5000 rpm for 20 minutes at 4° C. and then collected, and the sediment per liter culture of engineering bacteria was resuspended in 10 ml lysis buffer (50 mM Tris-HCl, 1 mM EDTA, 100 mM NaCl, pH8.0). The cells were broken up by ultrasonic, and then inclusion body was collected after centrifugation at 12000 rpm for 20 minutes at 4° C. Thereafter the sediment was resuspended in Solution I (20 mM Tris-HCl, 5 mM EDTA, 100 mM NaCl, pH8.5) containing 2% Triton X-100 (Sangon, Article No. T0694). Inclusion body was collected by centrifugation at 12000 rpm for 20 minutes at 4° C., the inclusion body was dissolved by 4M carbamide dispensed in Solution I and was then dialyzed against PB buffer (20 mM, pH7.0) 100 times in volume. After changing PB buffer 3 times, centrifugation was conducted at 12000 rpm for 20 minutes at 4° C. to remove sediment to get raw antigen. After the gelcolumn Sephacryl S-200 (America Amersham Biosciences Inc., USA) was equilibrated with the same PB buffer as above, said raw antigen was loaded. The outflow which contained target protein was collected and pooled. Subsequently, the combined outflow was loaded onto CM-Sepharose ion exchange column (Amersham Biosciences Inc., USA). The HCV antigen could be absorbed by CM-Sepharose, and the impurity protein was eluted by the PBS buffer (20 mM PB, 50 mM NaCl, pH7.0). Finally we eluted target protein with PBS buffer (20 mM PB, 500 mM NaCl, pH7.0), measured protein concentration and stored it at 4° C. or −20° C. for further use.

Example 2

Preparation of Secondary Antigen

1. Preparation of Biotinylated Secondary Antigen.

1.1 Enzymatic Biotinylation In Vivo 1.1.1 Co-Transformation and Expression

We amplified the gene encoding HCV antigen a.a.1-28 by PCR; the upstream primer thereof had BamHI site, and the downstream primer had BglII and EcoRI sites and a termination codon TAA therebetween. Thereafter we amplified gene segment L (SEQ ID NO. 3) encoding biotin acceptor protein by PCR; the upstream primer thereof had BamHI site, and the downstream primer had BglII site and EcoRI site and a termination codon TAA therebetween.

Gene coding a.a.1-28 cleaved by restriction endonuclease BamHI and EcoRI was cloned into P2-G expression vector cleaved by BglII and EcoRI endonuclease. The resulting positive clone P2-G-CORE (a.a.1-28) was named P2-HCVAg2, and its expression antigen was named HCVAg2. By cloning gene L cleaved by BamHI/EcoRI into the expression vector P2-G-CORE (a.a.1-28) treated by BglII/EcoRI endonucleases, we obtained the positive clone P2-G-CORE (a.a.1-28)-L, which ws named P2-X.

Besides peptide encoded by SEQ ID NO. 3 or its functional analogs, the biotin acceptor protein used in the present invention may also be biotin carboxyl carrier protein family or the functional segment thereof. We design primers to amplify the gene encoding biotin carboxyl carrier protein via PCR to take the place of gene L to accomplish cloning. The primers were as follows:

```
upstream primer 1                         (SEQ ID NO: 5)
5'-CGCGGATCCATGAAACTAAAGGTAACAGTCAACGGCA-3' upstream primer 2                         (SEQ ID NO: 6)
5'-GGCAGGATCCCCGGGTAAGGCAGGAGAGGGCGAGATTC-3' downstream primers                        (SEQ ID NO: 7)
5'-CGCGAATTCTTAAGATCTACCACCTTCTATTAACTCTAAAT
CCCCGATCTTGATGAG-3'
```

The upstream primer had BamHI site, and the downstream primer had BglII and EcoRI sites and a termination codon TAA therebetween. Taking the Pinpoint™ Xa-1 (Promega Corporation, USA, lot number V2031) as the template, we got gene Xal encoding segments of biotin carboxyl carrier protein (BCCP) of 128 amino acid residues by amplifying the upstream primer 1 and the downstream primer via PCR and got gene Xas encoding segments of biotin carboxyl carrier protein (BCCP) of 81 amino acid residues by amplifying the upstream primer 2 and the downstream primer via PCR. Like gene L, the encoded products thereof all had special lysine sites which could bind biotin. Upon comparison between the above three kinds of biotin acceptor proteins, we found Xal>Xas>L in regard of their capacity of binding the biotin. That is, biotin acceptor protein with intact segments and a large molecular weight had stronger ability to bind biotin. However, since damage to HCV antigen rose with the increase of the molecular weight, when the three kinds of proteins were chimeric at C-terminal of HCV protein as biotin acceptor protein, they had similar activity as secondary antigens after biotinylation. In the following experiments, we take gene L as the gene encoding biotin acceptor protein for detailed explanation.

We extracted the whole genome of *Escherichia coli* ER2566, and used it as the template to amplify *Escherichia coli* K12 BirA gene Y encoding biotin-[acetyl-CoA Carboxylase] synthetase by PCR. Amplification primers were as follows:

```
Primer 1:                                 (SEQ ID NO: 8)
5'-CCC GAA TTC ATG AAG GAT AAC ACC GTG CC-3'

Primer 2:                                 (SEQ ID NO: 9)
5'-GGG AAG CTT TTA TTT TTC GGC ACT ACG CAG
GGA TAT TTC ACC-3'
```

The upstream primer thereof had EcoRI site, while the downstream one had HindIII site. The amplified gene segment Y was cleaved by EcoRI/HindIII, and then cloned onto plasmid vector pET-32a(+) (Novagen, USA, lot number 70785-3) cleaved by the same endonucleases, from which we got pET-32a-Y.

The expression plasmid P2-X had the kanamycin resistant gene and PET-32a-Y had the ampicillin resistant gene. The two expression plasmids were shifted into the expression host ER2566 together by transformation respectively. The double resistant LB plate containing 100 ug/ml kanamycin and 100 ug/ml ampicillin (Sangon, Article No. A0741) was used to screen out the clone expressing both of the two proteins markedly, and the selected clone was transferred into 500 ml LB culture medium containing double-resistant agents kanamycin and ampicillin of the same concentration and D-biotin with a final concentration 20 uM (Sigma-Aldrich Corp. USA, Article No. B-4501) to shake culture to OD600 1.0 approximately. Thereafter IPTG whose final concentration was 0.5 mM was added to induce, at 37° C., 200 rpm for 4 hours. The cells were collected by centrifugation and the cells obtained from a liter bacterial culture were resuspended in 10 ml lysis buffer. The cells were broken up by ultrasonic. Supernatant was collected by centrifugation at 12000 rpm for 20 minutes at 4° C. Saturated ammonium sulfate was added into the supernatants up to 10%-30% (V/V) to precipitate. After that, the precipitate was re-dissolved in PB buffer (100 mM, pH7.0). Removal of the sediment was carried out by centrifugation at 12000 rpm for 10 minutes at 4° C. Avidin chromatography-column which contained SoftLink Soft Release Avidin resin was used to purify the target protein (Detailed purification process can be found in the instructions to Article No. V2012 by Promega Corporateion, USA). Purified biotinylated antigen was obtained by eluting with PB buffer (100 mM, pH 7.0) containing 5 mM D-biotin and then it was dialyzed against the PB buffer 100 times in volume to remove free biotin. The PB buffer was changed 3 times. After centrifugation, Supernatant was measured for protein concentration. The protein was stored at 4° C. or −20° C. for future use.

1.1.2 Polycistron Expression

The amplified gene fragment Y was cleaved by EcoRI/HindIII and then cloned onto the plasmid vector P2-X cleaved by the same endonuclease, from which we got a positive clone called P2-X-Y, namely the preferred expression plasmid for the secondary antigen of the present invention. The ER2566 strain (*Escherichia coli* ER2566/P2-HCVAg1) containing the plasmid had been deposited in China Center for Type Culture Collection (Wuhan University, Luojia hill, Wuchang district, Wuhan, Hubei province, China) in Jan. 21, 2005, with the access number of CCTCC M 205010. Because of the presence of a termination codon TAA between genes X and Y, genes X and Y composed a double-cistron under the effect of the same expression regulation element in P2-X-Y. The present invention applied the same method to construct the clone designed while screening the second antigen in this way of expression.

By transforming P2-X-Y into *Escherichia coli* ER2566, we got antigen HCVAg by expression and purification in accordance with the above method.

In this biotinylation method, we further tried adding an SD sequence between the termination codon of gene X and the initiation codon of gene Y (the specific method pertaining to the existing conventional technology of genetic engineering; for more details, see Tsao, K. L., et al., Gene, 169; P 59-64, 1996). Increase in the expression of protein encoded by gene Y could increase efficiency of biotinylation to some degree and further increase sensitivity of the kit of present invention.

1.1.3 Multi-Promoter Expression

Gene fragment Y amplified by PCR was cleaved by EcoRI/HindIII and then cloned onto the plasmid vector P1 cleaved by the same endonuclease, from which we got an expression plasmid called P1-Y. We designed a pair of positive and opposite primers at the upstream of T7 promoters and downstream of the terminator in P2-X as follows:

```
                                            (SEQ ID NO: 10)
Primer 1: 5'-GGCAGATCTTAATACGACTCACTATAGGG-3'

(SEQ ID NO: 11)
Primer 2: 5'-CCCAGATCTTGCTAGTTATTGCTCAGCGG-3'
```

The upsteam and downstream primers both contained BglII site. We amplified the whole T7 operator element containing gene X with the plasmid P2-X as a template. Then, by cloning the fragment cleaved by BglII into the expression vector P1-Y cleaved by the same endonuclease, we got an expression vector P1-X/Y with double promoters in which gene X and gene Y could perform transcription and translation under the regulation of their own operator elements respectively.

P1-X/Y was transformed into *Escherichia coli* ER2566 to express and purify the target protein.

1.1.4 Monocistron Expression

Gene Y was amplified by PCR with the total genome of ER2566 as the template. The primers for amplification are the following:

```
Primer 1                                    (SEQ ID NO: 12)
5'-CCC AGA TCT ATG AAG GAT AAC ACC GTG CC-3'

Primer 2                                    (SEQ ID NO: 13)
5'-GGG GAA TTC TTA TTT TTC GGC ACT ACG CAG
GGA TAT TTC ACC-3'
```

The upstream primer thereof had BglII site, while the downstream one had EcoRI site. The amplified gene segment Y was cleaved by BglII/EcoRI, and then cloned into plasmid vector P2-XY cleaved by the same endonucleases, from which we got an expression plasmid called P2-XY. Because the endonclease sites at 3'-terminal of gene X were BglII and EcoRI and there was a termination codon TAA therebetween, when P2-X was cleaved by BglII/EcoRI as the vector, the termination codon had been cleaved. So, the ligated gene Y and gene X constituted a monocistron, namely, chimeric expression gene XY.

P2-XY was transformed into *Escherichia coli* ER2566 to express and purify the target protein.

1.1.5 Co-Expression with Gene of Biotin Acetyl-CoA Carboxylase Synthetase in the Host P2-X was transformed to *Escherichia coli* ER2566 to express the target protein. Biotin-Acetyl-CoA Carboxylase synthetase originally expressed in ER2566 in vivo was used to partly biotinylate HCV antigen. Then the abovesaid SoftLink Soft Release Avidin resin was used for affinity purification.

In the above methods of enzymatic biotinylation in vivo, we further tried using a series of methods of inducing expression at low temperature, introducing molecular chaperones as the upstream cistron or foreign protein of the target protein, and so on to express HCV chimeric antigen and biotin Acetyl-CoA Carboxylase synthetase in soluble forms, which increased the efficiency of biotinylation to a certain degree. The methods applied herein to promote the expression of the gene engineering protein in soluble forms are just conventional methods that persons skilled in the art shall master, so will not be expatiated here.

1.2 Biotinylation In Vitro 1.2.1 Biotinylation of HCV Antigen In Vitro by Coupling Here, we illustrate the method by labeling the amino group of HCV antigen with sulfo-NHS-LC-biotin in the processes of:

1) taking 1 mg HCVAg2 antigen to dialyze against PBS containing 2M carbamide (100 Mm PB, 150 mM NaCl, pH7.2) overnight;

2) preparing the biotin solution: dissolving 2.2 mg sulfo-NHS-LC-biotin (PIERCE Inc., USA, Article No. 21335) in 0.4 ml ultrapure water (all water used in the present invention was ultrapure water), preparing immediately before use;

3) mixing the protein solution with the biotin solution at the mole ratio of 1:10-20, crosslinking them for 2 hours at 0-4° C. or for 30 minutes at room temperature;

4) dialyzing the reaction solution against PB buffer containing 0.05% SDS (100 mM PB, pH7.2) to eliminate the free biotin; and 5) adding glycerol with a final concentration of 50% and storing it at −20° C. for future use.

We can also choose different activated biotins to label different groups of HCV antigens (such as mercapto group, carboxyl, etc). Please refer to the product catalogue of PIERCE Inc. (USA).

1.2.2 In Vitro Biotinylation of HCV Antigen by Enzymatic Reaction

In the special buffer system that contained the ATP and D-biotin, biotin-Acetyl-CoA Carboxylase synthetase could also perform the in vivo function to label biotin on the HCV antigen with biotin acceptor protein.

We cloned biotin-Acetyl-CoA Carboxylase synthetase gene Y into pET-32a(+) for expression, then obtained a certain amount of the synthetase by Co-metal affinity chromatography column purification for in vitro biotinylating the HCV antigen containing biotin acceptor protein. The purified HCV antigen and a proper amount of biotin-Acetyl-CoA Carboxylase synthetase were further added to biotinylation buffer containing 10 mM ATP (Sangon, lot AB0020), 50 μM D-biotin, and 50 mM Bicine (Sangon, lot BB0266), 10 mM MgOAc (Sangon, lot MB0326), pH 8.3 for a biotinylation reaction for 12 hours at room temperature. Thereafter, the antigen was dialyzed against the PB buffer (100 mM, pH 7.0) 100 times in volume to remove free biotin. The PB buffer was changed 3 times. The supernatant obtained by centrifugation was purified with chromatography-column which contained SoftLink Soft Release Avidin resin. Purified biotinylation antigen was obtained by eluting with PB buffer (100 mM, pH 7.0) containing 5 mM D-biotin before the last dialysis.

1.3 Indirect Biotinylation

The following is an exemplification of indirect biotinylation of HCV antigen where His Tag stood for agent A and anti-His Tag monoclonal antibody (Novagen, USA, lot 70796-3) for agent B, and biotin was linked onto agent B.

The clone P2-G-CORE (a.a.1-28)-His obtained according to the above-mentioned methods was named P2-HCVAg3, which was transformed before being expressed and purified to give a corresponding antigen HCVAg3, wherein "His" represented His Tag. The same expression method applied to other chimeric polypeptides.

The biotin label of anti-His Tag monoclonal antibody was realized by the coupling reaction with the activated biotin using the same method as above. Enzyme labeled monoclonal antibody specifically bound to HCV antigen, thereby indirectly biotinylating HCV antigen.

The method of enzymatically labeling the binding partner of biotin (i.e. streptomycin) was $NaIO_4$ oxidation method: weighing out 10 mgHRP and dissolving it in 1 ml ultrapure water, slowly dripping 1 ml 5 mg/ml $NaIO_4$ (Sangon, lot ST1244) solution freshly prepared in ultrapure water, adding 0.05 ml 20% glycol (Sangon, lot E0582) solution therein after stirring it gently at room temperature free of light for 40 minutes, then stirring the resultant solution for 40 minutes free of light; thereafter adding immediately 1 ml 2.5 mg/ml streptomycin (Sangon, lot SE497) which had been dialyzed beforehand against 100 mM, pH 9.51 carbonate buffer for 2 hours, and then dialyzing it against 100 mM, pH9.51 carbonate buffer at 4° C. free of light overnight; the next day, dropping 0.1 ml freshly prepared 4 mg/ml $NaBH_4$ (Sangon, lot ST1268) solution into the mixture before mixing it evenly and standing it at 4° C. for 2 hours; then puffing the above solution into a dialysis bag and dialyzing it against PBS buffer (150 mM, pH7.4) at 4° C. overnight; and finally adding the enzyme protective agent and glycerol with a final concentration 50% therein, which was mixed evenly and stored at −20° C. free of light for future use.

If the secondary antigen was biotinylated HCV protein, the detection modes of this kit were as follows:

1) direct biotinylation mode: "a support-a primary antigen-an HCV antibody to be detected-a biotinylated secondary antigen-an HRP labeled streptomycin-an HRP substrate which develops color to form a recognizable signal"

2) Indirect biotinylation mode: "a support-a primary antigen-an HCV antibody to be detected-a secondary antigen (the chimeric expression product of His Tag and HCV protein)-a biotin labeled anti-His Tag monoclonal antibody-an HRP labeled streptomycin-an HRP substrate which develops color to form a recognizable signal".

2. Preparation for Secondary Antigen with Peptide Tag

We take the His Tag as an example to explain the method. In the examples above, we have constructed the clone P2-HCVAg3 with His Tag at C-terminal of HCV antigen and prepared the corresponding antigen HCVAg3. We have also tried using the above methods to chimerically attach His Tag at N-terminal, both terminals of the HCV protein or between NS3 and CORE, in which the four chimerics were all proved to be workable as the secondary antigen in present invention. Similarly, the biotin acceptor protein can also be chimerically attached using any of the four methods. Multiple chimerisms of the same tag or different tags can also improve sensitivity to certain degrees, which was confirmed in this invention as well. The techniques of gene chimerism and expression involved in the above methods all belong to conventional technology that persons skilled in the art shall master, and thus are not to be detailed any more.

Peptide tag can also be an HCV peptide fragment that is not included in the primary antigen and does not have a strong binding tendency. The principles and methods thereof are similar to those of His Tag as peptide tag, hence are not detailed herein.

The method of HRP labeling monoclonal antibody is similar to that of HRP labeling streptomycin. The main difference is that the mass label ratio of monoclonal antibody to HRP is 1:1-2 and the labeling time is 3-6 hours.

When the secondary antigen was the chimeric expression product of peptide tag and HCV protein, the detection mode of the present kit was: "a support-a primary antigen-an antibody-a secondary antigen (the chimeric expression product of peptide Tag and HCV protein)-an HRP labeled anti-a peptide tag monoclonal antibody-an HRP substrate whose color could be a recognizable signal"

Besides HRP, there are a lot of detectable agents to be selected, for example, enzymes such as alkaline phosphatase, β-galactosidase, etc; chemical illuminants such as acridine ester, etc; fluorescence agents such as fluorescein isothiocyanate, europium, europium nanometer particles, etc; radioactive agents such as $^{125}I$, etc; and colloids such as colloidal gold, latex, etc. Choosing different detectable agents is just to choose different immuno-diagnostic methods, i.e. enzyme linked immunosorbent assay, chemiluminescence Immunoassay, fluorescence immunoassay, time-resolved fluorescence Immunoassay, radioimmunoassay, gold labeled immunoassay and so on. Although the methods of detectable agent labeling streptomycin or monoclonal antibody and the respective immunoassays are different, they all belong to conventional experimental methods that persons skilled in the art shall master, and thus are not detailed any more.

We have also tried applying different ways of gene chimerism, different expression vectors and different purification methods to the primary antigen and the secondary antigen to increase the "gap" therebetween so as to improve the specificity of the present kit, which have all achieved certain effects. Those methods all pertain to conventional technology that persons skilled in the art shall master, and thus are not to be detailed here.

Example 3

Screening HCV Protein Segments in Primary Antigen and Secondary Antigen

First, we screened NS3 segment antigen to get clone P2-G (containing NS3 segment a.a.1201-1465) according to aforementioned method. The antigen NS3G after being expressed and purified, was detected for activity with indirect ELISA. Compared with C33C (NS3 a.a.1192-1457) from patent EP-A-0450931 of Chiron (USA) and D26 (NS3 a.a.1207-1488) from U.S. Pat. No. 6,096,319 of ROCHE (Switzerland), it was found that the specificity of NS3G was improved (see Table 1) and the sensitivity thereof was nearly the same. We further designed primers at a.a.1201±5 and a.a.1465±8 respectively and got clones P2-NS3(a.a.1196-1473), P2-NS3 (a.a.1206-1457), P2-NS3(a.a.1196-1457), and P2-NS3 (a.a.1206-1473). Those clones were detected for activity respectively after being expressed and purified, and it was found that the reactivity thereof was similar to NS3G. Finally, we chose a.a.1201-1465 (shortened as "G" hereinafter) as NS3 segment antigen of the present invention. The methods of screening all pertain to conventional experimental methods that persons skilled in the art shall master, and thus are not to be detailed here. For more details, please refer to the methods in U.S. Pat. No. 6,096,319.

TABLE 1

Specificity comparison of NS3G, C33C and D26
Result of detecting 3000 shares clinical negative

| Antigen name | positive (person) | negative (person) | Ratio of false positive |
|---|---|---|---|
| C33C | 13 | 2987 | 0.43% |
| D26 | 12 | 2988 | 0.40% |
| NS3G | 6 | 2994 | 0.20% |

In order to fundamentally solve the problem of non-specific reaction resulting from CORE segment protein, we designed different clones for CORE segments of the secondary antigen according to aforementioned methods. With HCVAg1 as the primary antigen for sensitivity detection, the kit with different CORE segments of the secondary antigen was found to have different sensitivity. See Table 2 for the differences.

TABLE 2

Difference of sensitivity of different core fragment for the secondary antigen

| Secondary antigen | sensitivity | Secondary antigen | sensitivity | Secondary antigen | sensitivity |
|---|---|---|---|---|---|
| a.a.1-23 | √ | a.a.1-21 | √ | a.a.1-17 | √ |
| a.a.6-48 | √ | a.a.7-48 | √ | a.a.10-48 | √ |
| a.a.1-6 | x | a.a.1-7 | x | a.a.1-10 | x |
| a.a.23-48 | x | a.a.21-48 | x | a.a.17-48 | x |

1) a.a.1-23 denote expression product of clone P2-G-CORE(a.a.1-23), the others are the same
2) If the sensitivity can get to the standard of commercial indirect diagnostic reagent (if there is no special explaination, the standard diagnostic reagent is Murex Anti-HCV 4.0), we represent "√", otherwise represent "x".

We designed similar clones for CORE segments of the primary antigen, and got similar results to Table 2 in sensitivity detection with HCVAg as the secondary antigen.

The above results show that in the sandwich method, when Core region of HCV primary or secondary antigen lacked segment a.a.6-23 of a complete sequence, further lacked segment a.a.7-21 of a complete sequence, and still further lacked segment a.a.10-17 of a complete sequence, the kit had rather low sensitivity.

We designed different clones for CORE segments of the secondary antigen. With HCVAg1 as the primary antigen for detection on the same kit system, the kit with different CORE segments of the secondary antigen was found to have different backgrounds. See Table 3 for the differences.

TABLE 3

Difference in background of different CORE fragments of the secondary antigen

| | CORE fragment | | | | | |
|---|---|---|---|---|---|---|
| | a.a. 1-90 | a.a.1-70 | a.a.1-59 | a.a.1-48 | a.a.1-28) | 3 × (a.a.1-28 |
| background | ++ | ++ | ++ | ++ | □ | ++ |

| | CORE fragment | | | |
|---|---|---|---|---|
| | a.a.32-90 | a.a.32-70 | a.a.32-48 | a.a.1-28&49-70 |
| background | ++ | ++ | ++ | ++ |

TABLE 3-continued

Difference in background of different CORE fragments of the secondary antigen

| | CORE fragment | |
|---|---|---|
| | a.a.49-70 | a.a.49-70 |
| background | + | ☐ |

1) a.a.1-90 represent the expression product of clone P2-G-CORE(a.a.1-90), the others are the same
2) 3 × (a.a.1-28) represent the expression product of clone P2-G-CORE (a.a.1-28)-L-Y; 3 × represent three times fusion of a.a.1-28 gene
3) a.a.49-70 represent the expression product of P2-L-CORE (a.a.49-70)-G-Y
4) ++ represent higher background, + represent high background, – represent normal background.

The above results show that the first epitope a.a.1-28 (shortened as "a"), the second epitope a.a.32-48(shortened as "b"), and the third epitope a.a.49-70 (shortened as "c") of HCV CORE segment all had binding tendency, wherein b had the strongest. When the secondary antigen had two or more of the above three segments, and said two or more segments were subject to sufficient exposure, the kit tended to have high background.

With similar experiments on CORE segments of the primary antigen, it was found that the background of the kit tended to rise with the lengthening of CORE at C-terminal, but not so obvious as that of the secondary antigen. That is, the high background of HCV sandwich kit arose mainly from the CORE protein segment of the secondary antigen.

As shown by the results of the experiments, when the CORE segment of HCV antigen, particulary the secondary antigen, contained segment a.a.32-48 of a complete sequence, further segment a.a.29-59 of a complete sequence, still further segment a.a.29-70 of a complete sequence, and even further segment a.a.29-90 of a complete sequence, the Kit tended to have rather high background.

Therefore, the HCV CORE protein of the present invention was characterized in: a segment containing a.a.10-17 complete sequence, further a segment containing a.a.7-21 complete sequence, still further a segment containing a.a.6-23 complete sequence, and excluding a.a.29-90 complete sequence, further excluding a.a.29-70 complete sequence, still further excluding a.a.29-59 complete sequence, and even further excluding a.a.32-48 complete sequence. Said protein segments might have mutation(s) while keeping antigenicity and binding ability unchanged.

Furthermore, to confirm that high background is caused by the binding ability of CORE antigen, we conducted the following experiments:

1) Validating the homologous binding: for which we chose HCVAg1 as the primary antigen.

2) Validating the heterogenous binding: for which we chose HIVgp41 antigen, treponema pallidum Tp17 antigen, bovine albumin (component V) (BSA, Shanghai Weiqun Bio-technology Co., Ltd) as the primary antigen respectively.

For detection, we chose the expression product of P2-G-CORE(a.a.1-70)-L-Y as the secondary antigen, and selected specimens to be detected from human HCV negative serum (all the HCV negative or positive serum applied the present invention were from healthy group), 20% newborn calf serum, 1% BSA, and non-analyte specimens (specimen diluent in place of the specimens) respectively. See Table 4 for the results.

TABLE 4

| Corroboration experiments of aggregation trend of homologous and heterogenous CORE fragment. | | | | |
|---|---|---|---|---|
| | Primary antigen | | | |
| Analyte sample | HCVAg1 | HIVgp41 | Tp17 | BSA |
| HCV negative serum | ++ | + | + | + |
| 20% NBS | ++ | + | + | + |
| 1% BSA | ++ | + | + | + |
| Sample diluent | ++ | + | + | + |

Note□
++ represent higher background,
+ represent high background

When we only used the expression product of P2-G as the primary antigen, and the expression product of P2-G-L-BirA or the expression product of P2-G-CORE(a.a.1-70)-L-Y as the secondary antigen respectively, the former, i.e., with only NS3 antigen for sandwich, no longer suffered from the problem of high background while the latter still suffered from high background.

It can be seen from the results above that high background of the kit for detecting an HCV antibody by the double-antigen sandwich method was caused by the tendency to homologous and heterogeneous binding in CORE antigen in such a reaction mode as "a support-a primary antigen-a secondary antigen-a label-a recognizable signal".

The present invention selected CORE segment of HCV antigen for the sandwich method on the principles that as long as activity was guaranteed, the shorter the segment, the better, and that N-terminal was most preferred.

By said screening, we confirmed that the CORE segment of the primary antigen was a.a.2-59 and the CORE segment of the secondary antigen was a.a.1-28.

With activity of the antigen guaranteed, we continued to try further shortening the CORE segments of the primary antigen and the secondary antigen, thereby making some improvements on the background of the kit as well as on the activity of NS3 antigen.

Example 4

Determination on the Molecular Weight of Peptide Tags as Heterologous Protein To research the effect of peptide tags as heterologous proteins on the activity of HCV antigen, the present invention designed clones for fusing peptide tags of different sizes at N-terminal and C-terminal of HCV protein. The methods for constructing the clones and expressing and purifying protein could be found in Examples 1 and 2 for reference. 100 HCV positive sera diluted with two shares of negative serum of healthy adults respectively were detected with HCVAg1 as the primary antigen, the purified antigens of the above clones as the secondary antigens, and anti-His Tag monoclonal antibodies labeled with HRP as the label. The controls were selected from the HCV indirect diagnostic reagents (InTec Products, Inc. (Xiamen)) and the Murex Anti-HCV 4.0 kit of Abbott. The results are shown in Table 5 and Table6.

TABLE 5

The effect of N-terminal peptide tags to activity of HCV antigen
The number of serum positive reaction to different reagents

| The secondary antigen | N-terminal peptide tags approximate MW | dilute multiple of the serum | | | | |
|---|---|---|---|---|---|---|
| | | 1 | 25 | A50 | 100 | 200 |
| HCVAg-N1 | 1KD | 100 | 100 | 98 | 96 | 80 |
| HCVAg-N2 | 2KD | 100 | 100 | 98 | 95 | 79 |
| HCVAg-N3 | 5KD | 100 | 99 | 96 | 92 | 72 |
| HCVAg-N4 | 10KD | 100 | 93 | 90 | 81 | 60 |
| HCVAg-N5 | 15KD | 100 | 89 | 80 | 62 | 41 |
| HCVAg-N6 | 20KD | 100 | 88 | 76 | 55 | 39 |
| indirect HCV reagent (InTec Products, Inc. (Xiamen)) | | 100 | 75 | 62 | 40 | 28 |
| Murex Anti-HCV 4.0 | | | 100 | 85 | 73 | 50 | 37 |

Remarks:
HCVAg-N1 was expression product of P2-His-G-CORE(a.a.1-28)□
HCVAg-N2 was expression product of P2-His-T7-G-CORE(a.a.1-28)□
HCVAg-N3 was expression product of pET-30a-G-CORE(a.a.1-28)□
HCVAg-N4 was expression product of P2-His-Xas-G-CORE(a.a.1-28)□
HCVAg-N5 was expression product of P2-His-Xal-G-CORE(a.a.1-28)□
HCVAg-N6 was expression product of P2-His-Xas-Xas-G-CORE(a.a.1-28).

TABLE 6

| The effect of C-terminal peptide tags to HCV antigen The number of serum positive reaction to different reagents | | | | | | |
|---|---|---|---|---|---|---|
| The secondary antigen | C-terminal peptide tags approximate MW | dilute multiple of the serum 1 | 25 | 50 | 100 | 200 |
| HCVAg-C1 | 1KD | 100 | 100 | 99 | 97 | 84 |
| HCVAg-C2 | 2KD | 100 | 100 | 99 | 97 | 83 |
| HCVAg-C3 | 5KD | 100 | 100 | 97 | 94 | 80 |
| HCVAg-C4 | 10KD | 100 | 99 | 94 | 89 | 71 |
| HCVAg-C5 | 15KD | 100 | 96 | 90 | 81 | 61 |
| HCVAg-C6 | 20KD | 100 | 94 | 87 | 74 | 49 |
| HCVAg-C7 | 30KD | 100 | 89 | 78 | 59 | 39 |
| indirect HCV reagent (InTec Products, Inc.(Xiamen)) | | 100 | 72 | 59 | 37 | 26 |
| Murex Anti-HCV 4.0 | | 100 | 83 | 69 | 45 | 35 |

Remark:
HCVAg-C1 was expression product of P2-G-CORE(a.a.1-28)-His□
HCVAg-C2 was expression product of P2-G-CORE(a.a.1-28)-T7-His□
HCVAg-C3 was expression product of P2-G-CORE(a.a.1-28)-L-L-His□
HCVAg-C4 was expression product of P2-G-CORE(a.a.1-28)-Xas-His□
HCVAg-C5 was expression product of P2-G-CORE(a.a.1-28)-Xal-His□
HCVAg-C6 was expression product of P2-G-CORE(a.a.1-28)-Xas-Xas-His□
HCVAg-C7 was expression product of P2-G-CORE(a.a.1-28)-Xas-Xas-Xas-His.

This experiment confirmed the loss of activity in HCV antigen caused by the heterologous protein. It can be seen from the results that the larger the heterologous peptides, the greater the loss of activity in HCV antigens, which was particularly prominent in fusion at N-terminal. It was later confirmed that the same applied to the primary antigen. In this regard, the present invention selected the heterologous protein of HCV primary and secondary antigens with such a standard that the smaller molecular weight of the heterologous protein, the better, where the standard of molecular weight could be optimized step by step to less than 30 KD□20 KD□15 KD□10 KD and 5 KD.

When selecting a secondary antigen with the combination of biotin and biotin acceptor protein as tag, we should also consider the ability of biotin acceptor protein to bind biotin, to ensure that the molecular weight of biotin acceptor protein is as small as possible without affecting biotinylation. Therefore, the molecular weight of biotin acceptor protein is not completely limited by above restrictions.

Example 5

Production and Use of the Kit of the Present Invention

1. Biotinylating HCV Antigen as Secondary Antigen

Diluting the HCV primary antigen with carbonate buffer (50 mM, pH9.51, containing 0.2‰ SDS) by a certain ratio; adding 100 ul of the diluted liquid to each well of ELISA plate (irradiation ELISA plate by Jincanhua Industrial Co., Ltd, Shenzhen, China), and coating for 24 hours at 4° C.; the next day, using PBST (10 mM PB, 150 mM NaCl, 0.05% Tween-20, pH7.4) washing buffer to wash the plate twice, and then desiccating the wells by patting; adding 120 ul pH7.4, 10 mM PB blocking buffer into each well, which contained 30% newborn calf serum (Beijing Yuanheng Shengma Biotechnology Researching Institute), 8% sucrose, 5‰ casein (Sigma-Aldrich Corp. (USA), Article No. C-8645), 1‰ β-mercaptoethanol (Sangon, Article No. M0482), 150 mM NaCl, and then blocking for 2 hours at 37° C.; discarding liquid in wells and desiccating the wells by patting; after being dried by air in room equipped with draft equipment where temperature was 20-25° C. and humidity was 55%-65%, packaging the plate in aluminum film bag with desiccant, thereby completing the coating.

The testing can be performed according to two-step method or three-step method as listed below. P s1.1 Two-Step Method:

Adding into the coated ELISA plate 50 ul specimen to be detected, negative (healthy adult negative serum), positive (HCV antibody positive serum) control; adding into each well of the plate 50 ul pH7.4, 20 mM PB buffer, which contained 1‰ β-mercaptoethanol, 0.5‰ TritonX-100, 20% newborn calf serum, 5‰ casein, 150 mM NaCl and biotinylated HCV secondary antigen (diluted before using) diluted with a certain ratio; incubating for 60 minutes at 37° C.; washing each well five times with the PBST washing buffer; desiccating the wells by patting; adding into each well of the reaction plate 100 ul pH7.4 20 mM PB buffer, which contained 1‰ casein, 20% newborn calf serum and emzyme-labeled streptavidin (diluted before using) diluted by a certain ratio, incubating for 30 minutes at 37° C.; washing each well five times with PBST washing buffer; desiccating the wells by patting; respectively adding 50 ul color development reagent A and color development reagent B into each well, wherein color development reagent A contained 0.5‰ hydrogen peroxide carbamide (Sangon, Article No. UB1753), 4.76‰ sodium acetate trihydrate, 0.9‰ acetic acid and color development reagent B contained 0.32‰ TMB (Sangon, Article No. TB0514), 5 mM citric acid, 0.5 mM EDTA-2Na, 5% methanol, 2‰ N,N-Dimethyl formamide; and avoiding light to develop color for 30 minutes at 37° C.; adding 50 ul stop solution which contained 2M sulfuric acid into each well to terminate reaction; after adjusting the Zero with blank control in 450 nm wavelength (reference wavelength was 630 nm) of the micro-plate reader, using it to read OD value; calculating cutoff value (COV): COV□mean of negative control OD value×2.0 (if negative control OD value <0.075, using 0.075; if negative control OD value >0.075, using actual OD value); if the OD value of the specimen to be detected ≧COV, the specimen was positive; if the OD value of the specimen to be detected OD value□COV, the specimen was negative.

1.2 Three-Step Method

Adding into each well of the coated plate 50 ul specimen diluent buffer (20 mM pH7.4 PB, containing 1% β-mercaptoethanol, 1‰ TritonX-100, 20% newborn calf serum); adding 50 μl specimen to be detected, negative and positive control; incubating for 60 minutes at 37° C.; thereafter washing the plate five times with PBST washing buffer; desiccating the wells by patting thereafter; adding 100 ul 20 mM pH7.4 PBS containing 1% β-mercaptoethanol, 1‰ TritonX-100, 20% newborn calf serum, 150 mM NaCl and biotinylated HCV antigen diluted at a certain ratio (diluted just before use) to each well; incubating for 30 minutes at 37° C.; and the subsequent processes being identical to those in two-step method;

Dilution ratio of biotinylated HCV antigen and enzyme labeled streptoavidin should be adjusted in accordance with the actual circumstances so as to reach the best effect. The dilution ratio of reactants and the reaction time for each step can also be adjusted in production to ensure detection effect, shorten detection time and raise working efficiency. Belonging to conventional testing means for persons skilled in the art, such adjustments are not detailed herein.

The three-step method was preferred in this invention.

2. HCVAg3 Antigen with His Tag as Secondary Antigen

For details of the method, please refer to production and use of the kit in Biotinylating HCV antigen as secondary antigen.

Example 6

Evaluation on the Kit of the Present Invention (1) Sensitivity

By comparing the sensitivity of the sandwich kit that used biotinylated HCV protein as the secondary antigen with that of the commercial indirect ELISA kit, we got similar results to those in Table 6, showing that both the kit of the present invention and the commercial indirect ELISA kit were of statistic significance (P<0.05) to the sensitivity difference of serum reactions at various dilution levels. It is evident that the sensitivity of the kit of the present invention has been improved a lot over the indirect reagent.

(2) Specificity

By means of three-step specific recognition, the present invention was greatly improved over the indirect reagent of only one-step specific recognition. Upon detection of 3000 shares of clinical negative serum using the kit of the present invention and an HCV indirect kit of InTec Products, Inc. (Xiamen) respectively, it is found that the ratio of false positive serum of the former was 0.067% while that of the latter was 0.67%. Upon further detection of the false positive serum of the latter using the Murex Anti-HCV 4.0 indirect ELISA kit, it is found that the ratio was 0.4%.

(3) Suspicious Serum

Through screening, we got 12 shares of suspicious serum which were diagnosed to be positive by our own indirect reagent, suspicious by HCV RIBA confirmatory reagent (Genelabs Diagnostics Pte Ltd, Singapore, Article No. 11130-018), and negative by PCR detection (COBAS Ampliscreen™ HCV 2.0 of ROCHE, Switzerland). The suppliers of the suspicious serum had no clinical hepatitis symptom (data shown in Table 7). Except C5, 11 shares of the serum were detected negative by the sandwich method, and positive by the indirect method using the primary and secondary antigens employed by the sandwich method as coating antigens, while RIBA results show that NS4 was positive alone. But neither of the above two antigens had an NS4 segment. It can thus be concluded that the 11 shares of serum were false positive as detected by own indirect reagent. C5 was similar to the 11 serum. Although it was detected positive in the sandwich method, since the OD value shown in the reaction of the sandwich method was markedly lower than in the indirect method, it can be inferred that C5 was false positive in both the sandwich and the indirect methods. In the same way, the other 10 serum other than C4 and C6 were supposed to be false positive in Murex Anti-HCV 4.0 kit. In a word, the kit of the present invention is more accurate in detecting suspicious serum than the existing commercial reagent and our own indirect reagent.

TABLE 7

Result of detection suspicious serum (all be negative) in the present invention

| sample | Kit of the present invention | coating antigen indirect ELISA detection | biotin labeled antigen indirect ELISA | Murex Anti-HCV 4.0 | Genelabs HCV BLOT Version 3.0 | PCR |
|---|---|---|---|---|---|---|
| C1 | □ | + | + | + | NS4+ | □ |
| C2 | □ | + | + | + | NS4+ | □ |
| C3 | □ | + | + | + | NS4+ | □ |
| C4 | □ | + | + | □ | NS3-1+ | □ |
| C5 | weak+ | + | + | + | NS4+ | □ |
| C6 | □ | + | + | □ | NS3-1+ | □ |
| C7 | □ | + | + | + | NS4+ | □ |
| C8 | □ | + | + | + | NS4+ | □ |
| C9 | □ | + | + | + | NS4+ | □ |
| C10 | □ | + | + | + | NS4+ | □ |
| C11 | □ | + | + | + | NS4+ | □ |
| C12 | □ | + | + | + | NS4+ | □ |

Note:
+ positive;
□ negative

29

(4) Repeatability 240 shares of negative specimens to be detected and 240 shares of positive specimens to be detected were detected at different times in different batches and by different operators repeatedly to check repeatability in the detection results on the kit of the present invention. The results show 100% repeatability in the negative and positive assessment of the kit of the present invention, which indicates that the detection results by the present method have good reproducibility and reliable assessment.

(5) Stability

A whole set of reagents (including coated ELISA plate, specimen diluent, secondary antigen, secondary antigen diluent, enzyme-labeled streptavidin, enzyme diluent, negative control, positive control, color development reagents A and B, and stop solution) was placed under 37° C. for 72 hours, and then taken out for detection of negative and positive quality control serum under the same condition as for detection of negative and positive quality control serum in the reagents stored under 4° C. at the same time. The results are shown in Table 8. Experiments indicate that the kit of the present invention has good stability.

30

TABLE 8

Experiment result of the present invention kit stability

| store condition | linearity | CV value | mean of positive control | mean of negative positive control | negative and positive quality control serum |
|---|---|---|---|---|---|
| store at 4° C. | 99.90% | 9% | 1.613 | 0.023 | OD value has not obviously |
| check after 72 hours at 37° C. | 99.90% | 8.5% | 1.516 | 0.018 | difference in the two condition sample |

(6) Precision 10 or more-well Repeated detection was carried out in parallel time and again on the same known positive specimen on the same reaction plate to give an OD value of each well, from which it was calculated that the coefficient of variation values were all lower than 15%, which indicates the present kit has good precision.

I claim:

1. A kit for detecting an anti-hepatic C virus (HCV) antibody comprising:

a primary HCV antigen consisting of a NS3 segment consisting of the amino acids encoded by nucleotides 16 to 810 of SEQ ID NO: 2, and a CORE segment consisting of the amino acids encoded by nucleotides 4 to 177 of SEQ ID NO: 1, the primary HCV antigen being coated on a solid support;

a secondary HCV antigen consisting of a NS3 segment consisting of the amino acids encoded by nucleotides 16 to 810 of SEQ ID NO: 2, and a CORE segment consisting of the amino acids e encoded by nucleotides 1 to 84 of SEQ ID NO: 1, the secondary HCV antigen being conjugated to biotin; and a label, wherein said the label is streptavidin marked with horseradish peroxidase (HRP).

* * * * *

SEQUENCE LISTING

```
<160> NUMBER OF SEQ ID NOS: 16

<210> SEQ ID NO 1
<211> LENGTH: 270
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Hepatitis C Virus

<400> SEQUENCE: 1
atgagcacga accctaaacc tcaaagaaaa accaaacgta acaccaaccg ccgcccacag      60
gacgtcaagt tcccgggcgg tggtcagatc gttggtggag tttacctgtt gccgcgcagg     120
ggccccaggt tgggtgtgcg cgcgactagg aagacttccg agcggtcaca acctcgtgga     180
aggcgacaac ctatccccaa ggctcgccgt cccgagggca ggacctgggc tcagccctgg     240 taccctggc ccctctatgg caatgagggc                                       270

<210> SEQ ID NO 2
<211> LENGTH: 834
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Hepatitis C Virus

<400> SEQUENCE: 2
atccctgtgg agaacctaga aactaccacg cggtctccgg ttttcacaga caactcatcc      60
cccccggccg taccgcagac attccaagtg gcccatctac acgctcctac tggcagcggc     120
aagagcacta aagtgccggc tgcatatgcg gcccaagggt acaaggtgct cgtcctgaac     180
ccgtccgttg ccgccacctt aggttttggg gcgtatatgt ctaaggcaca tggtatcgac     240
cctagcgtca ggaccggggt aaggaccatc accacgggta gccccatcac gtactccacc     300
```

```
tatggcaagt tccttgctga tggtggttgc tctgggggtg cctatgacat tataatatgt    360
gatgagtgcc attcaactga ctcgactact atcttgggca tcggcacggt cctggaccaa    420
gcggagacgg ctggagcgcg gcttgtcgtg ctcgccaccg ctacgcctcc gggatcggtc    480
accgtgccac atcccaacat ccaggaggtg gccctgtcca atactggaga gatcccsttc    540
```
(Note: re-reading line 540)
```
accgtgccac atcccaacat ccaggaggtg gccctgtcca atactggaga gatccccttc    540
tatggtaaag ccatccccat cgaggccatc agggggggaa ggcatctcat tttctgccac    600
tccaagaaga agtgtgacga gctcgctgca aagctatcat ccctcggact caacgctgtg    660
gcgtactacc ggggtcttga tgtgtccgtc ataccatcta gcggagacgt cgttgtcgtg    720
gcaacagacg ctctaatgac gggctttacc ggcgactttg actcagtgat cgactgtaac    780
acgtgcgtca cccagacagt cgatttcagc cttgacccta ccttcaccat tgag          834
```

<210> SEQ ID NO 3
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Gene coding biotin receptor protein

<400> SEQUENCE: 3

```
atggctggtg gtttaaacga catctttgaa gctcagaaaa tcgaatggca tgaagacacc     60
ggtggctct                                                            69
```

<210> SEQ ID NO 4
<211> LENGTH: 966
<212> TYPE: DNA
<213> ORGANISM: Escherichia coli

<400> SEQUENCE: 4

```
atgaaggata caccgtgcc actgaaattg attgccctgt tagcgaacgg tgaatttcac      60
tctggcgagc agttgggtga aacgctggga atgagccggg cggctattaa taaacacatt    120
cagacactgc gtgactgggg cgttgatgtc tttaccgttc cgggtaaagg atacagcctg    180
cctgagccta tccagttact taatgctaaa cagatattgg gtcagctgga tgcggtagt    240
gtagccgtgc tgccagtgat tgactccacg aatcagtacc ttcttgatcg tatcggagag    300
cttaaatcgg gcgatgcttg cattgcagaa taccagcagg ctggccgtgg tcgccggggt    360
cggaaatggt tttcgccttt tggcgcaaac ttatatttgt cgatgttctg gcgtctggaa    420
caaggcccgg cggcggcgat tggtttaagt ctggttatcg gtatcgtgat ggcggaagta    480
ttacgcaagc tgggtgcaga taagttcgt gttaaatggc ctaatgacct ctatctgcag    540
```
(re-reading 540)
```
ttacgcaagc tgggtgcaga taagttcgt gttaaatggc ctaatgacct ctatctgcag    540
gatcgcaagc tggcaggcat tctggtggag ctgactggca aaactggcga tgcggcgcaa    600
atagtcattg gagccgggat caacatggca atgcgccgtg ttgaagagag tgtcgttaat    660 cagggtgga tcacgctgca ggaagcgggg atcaatctcg atcgtaatac gttggcggcc    720
```
(re-reading 720)
```
cagggtgga tcacgctgca ggaagcgggg atcaatctcg atcgtaatac gttggcggcc    720
atgctaatac gtgaattacg tgctgcgttg gaactcttcg aacaagaagg attggcacct    780
tatctgtcgc gctgggaaaa gctggataat tttattaatc gcccagtgaa acttatcatt    840
ggtgataaag aaatatttgg catttcacgc ggaatagaca aacaggggc tttattactt    900 gagcaggatg gaataataaa accctggatg ggcggtgaaa tatccctgcg tagtgcagaa    960
aaataa                                                               966
```

<210> SEQ ID NO 5

```
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Upstream primer 1 of the biotin binding protein
      L

<400> SEQUENCE: 5
cgcggatcca tgaaactaaa ggtaacagtc aacggca                              37

<210> SEQ ID NO 6
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Upstrain primer 2 of the biotin binding protein
      L

<400> SEQUENCE: 6
ggcaggatcc ccgggtaagg caggagaggg cgagattc                             38

<210> SEQ ID NO 7
<211> LENGTH: 57
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Downstream primer of the biotin binding protein
      L

<400> SEQUENCE: 7
cgcgaattct taagatctac caccttctat taactctaaa tccccgatct tgatgag       57

<210> SEQ ID NO 8
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Upstream primer of gene coding
      biotin-[acetyl]-CoA carboxylase] synthetase BirA

<400> SEQUENCE: 8
cccgaattca tgaaggataa caccgtgcc                                       29

<210> SEQ ID NO 9
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Downstream primer of gene coding
      biotin-[acetyl-CoA carboxylase] synthetase BirA

<400> SEQUENCE: 9
gggaagcttt tattttttcgg cactacgcag ggatatttca cc                       42
```

```
<210> SEQ ID NO 10
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Upstream primer of the T7 Promoter in vector
      plasmid P1

<400> SEQUENCE: 10
ggcagatctt aatacgactc actataggg                                   29

<210> SEQ ID NO 11
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Downstream primer of the T7 Promoter in vector
      plasmid P1

<400> SEQUENCE: 11
cccagatctt gctagttatt gctcagcgg                                   29

<210> SEQ ID NO 12
<211> LENGTH: 29
<212> TYPE: DNA
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Upstream primer of gene coding
      biotin-[acetyl-CoA carboxylase] synthetase BirA (gene Y)

<400> SEQUENCE: 12
cccagatcta tgaaggataa caccgtgcc                                   29

<210> SEQ ID NO 13
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Downstream primer of gene coding
      biotin-[acetyl-CoA carboxylase synthetase BirA (gene Y)

<400> SEQUENCE: 13
ggggaattct tattttttcgg cactacgcag ggatatttca cc                   42

<210> SEQ ID NO 14
<211> LENGTH: 795
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Hepatitis C Virus

<400> SEQUENCE: 14
ctagaaacta ccacgcggtc tccggttttc acagacaact catccccccc ggccgtaccg    60
cagacattcc aagtggccca tctacacgct cctactggca gcggcaagag cactaaagtg   120
```

-continued

```
ccggctgcat atgcggccca agggtacaag gtgctcgtcc tgaacccgtc cgttgccgcc      180
accttaggtt ttggggcgta tatgtctaag gcacatggta tcgaccctag cgtcaggacc      240
ggggtaagga ccatcaccac gggtagcccc atcacgtact ccacctatgg caagttcctt      300
gctgatggtg gttgctctgg gggtgcctat gacattataa tatgtgatga gtgccattca      360
actgactcga ctactatctt gggcatcggc acggtcctgg accaagcgga gacggctgga      420
gcgcggcttg tcgtgctcgc caccgctacg cctccgggat cggtcaccgt gccacatccc      480
aacatccagg aggtggccct gtccaatact ggagagatcc ccttctatgg taaagccatc      540
cccatcgagg ccatcagggg gggaaggcat ctcattttct gccactccaa gaagaagtgt      600
gacgagctcg ctgcaaagct atcatccctc ggactcaacg ctgtggcgta ctaccggggt      660
cttgatgtgt ccgtcatacc atctagcgga gacgtcgttg tcgtggcaac agacgctcta      720
atgacgggct ttaccggcga ctttgactca gtgatcgact gtaacacgtg cgtcacccag      780
acagtcgatt tcagc                                                      795
```

<210> SEQ ID NO 15
<211> LENGTH: 174
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Hepatitis C Virus

<400> SEQUENCE: 15

```
agcacgaacc ctaaacctca aagaaaaacc aaacgtaaca ccaaccgccg cccacaggac       60
gtcaagttcc cgggcggtgg tcagatcgtt ggtggagttt acctgttgcc gcgcaggggc      120
cccaggttgg gtgtgcgcgc gactaggaag acttccgagc ggtcacaacc tcgt            174
```

<210> SEQ ID NO 16
<211> LENGTH: 969
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Chimeric

<400> SEQUENCE: 16

```
ctagaaacta ccacgcggtc tccggttttc acagacaact catccccccc ggccgtaccg       60
cagacattcc aagtggccca tctacacgct cctactggca gcggcaagag cactaaagtg      120
ccggctgcat atgcggccca agggtacaag gtgctcgtcc tgaacccgtc cgttgccgcc      180
accttaggtt ttggggcgta tatgtctaag gcacatggta tcgaccctag cgtcaggacc      240
ggggtaagga ccatcaccac gggtagcccc atcacgtact ccacctatgg caagttcctt      300
gctgatggtg gttgctctgg gggtgcctat gacattataa tatgtgatga gtgccattca      360
actgactcga ctactatctt gggcatcggc acggtcctgg accaagcgga gacggctgga      420
gcgcggcttg tcgtgctcgc caccgctacg cctccgggat cggtcaccgt gccacatccc      480
aacatccagg aggtggccct gtccaatact ggagagatcc ccttctatgg taaagccatc      540
cccatcgagg ccatcagggg gggaaggcat ctcattttct gccactccaa gaagaagtgt      600
gacgagctcg ctgcaaagct atcatccctc ggactcaacg ctgtggcgta ctaccggggt      660
```

-continued

```
cttgatgtgt ccgtcatacc atctagcgga gacgtcgttg tcgtggcaac agacgctcta       720
atgacgggct ttaccggcga ctttgactca gtgatcgact gtaacacgtg cgtcacccag       780
acagtcgatt tcagcagatc catgagcacg aaccctaaac ctcaaagaaa aaccaaacgt       840
aacaccaacc gccgcccaca ggacgtcaag ttcccgggcg gtggtagatc catggctggt       900
ggtttaaacg acatctttga agctcagaaa atcgaatggc atgaagacac cggtggctct       960
agatcttaa                                                               969
```